United States Patent [19]
Breu et al.

[11] Patent Number: 6,133,442
[45] Date of Patent: *Oct. 17, 2000

[54] ARYL- AND HETARYL-SULFONAMIDE DERIVATIVES, THEIR PREPARATION AND THEIR USE AS ENDOTHELIN ANTAGONISTS

[75] Inventors: Volker Breu, Schliengen, Germany; Kaspar Burri, Binningen, Switzerland; Jean-Marie Cassal, Mulhouse, France; Martine Clozel, St. Louis, France; Georges Hirth, Huningue, France; Bernd-Michael Löffler, Oberrimsingen, Germany; Marcel Müller, Frenkendorf, Switzerland; Werner Neidhart, Hagenthal le Bas, France; Henri Ramuz, Birsfelden, Switzerland

[73] Assignee: Hoffmann-La Roche Inc., Nutley, N.J.

[*] Notice: This patent is subject to a terminal disclaimer.

[21] Appl. No.: 09/263,034

[22] Filed: Mar. 5, 1999

Related U.S. Application Data

[62] Division of application No. 08/860,985, filed as application No. PCT/EP95/04762, Dec. 4, 1995, Pat. No. 5,962,682.

[30] Foreign Application Priority Data

Dec. 20, 1994 [CH] Switzerland .............................. 3838/94
Oct. 31, 1995 [CH] Switzerland .............................. 3079/95

[51] Int. Cl.$^7$ ................................................. C07D 213/75
[52] U.S. Cl. .......................... 544/123; 544/124; 544/131; 544/148; 544/159; 544/316; 544/364; 544/365; 544/377; 544/388; 546/194; 546/226; 546/261; 546/265; 546/283.7; 546/291; 546/292; 546/293; 546/300; 546/309; 546/324; 546/337; 548/252; 549/414; 549/416; 549/438
[58] Field of Search ............................... 546/283.7, 291, 546/292, 293, 300; 544/123, 124

[56] References Cited

U.S. PATENT DOCUMENTS 4,117,151  9/1978  Descamps et al. .................. 424/285
4,902,698  2/1990  Cooper .................................. 514/351
5,270,313  12/1993 Burri et al. ............................ 514/252
5,292,740  3/1994  Burri et al. ............................ 514/256
5,420,129  5/1995  Breu et al. ............................. 514/252
5,962,682  10/1999 Breu et al. ............................. 544/123

FOREIGN PATENT DOCUMENTS 0 472053   2/1992   European Pat. Off. .
0 526708   2/1993   European Pat. Off. .
0 569193   11/1993  European Pat. Off. .
601386     6/1994   European Pat. Off. .
0 658548   6/1995   European Pat. Off. .
WO 95/26957 10/1995 WIPO .

OTHER PUBLICATIONS

Clozel, et al., Nature (1993) 365, pp. 759–761.
Biochem. Biophys. Res. Commun. (1994) 201, pp. 228–234 Chan M.F. et al.

Arzneimittel–Forschung, vol. 15, No. 11 (Nov. 1965) pp. 1309–1317, Kruger–Thiemer, et al., "Die antibakterielle Wirkung des nicht eiweissgebundenen Anteils der Sulfanilamide im menschlichen Plasmawasser", English translation.

Journal of Medicinal chemistry, vol. 35, No. 9, (May 1992) pp. 1493–1508, Doherty, A.M.

Primary Examiner—Richard L. Raymond
Attorney, Agent, or Firm—George W. Johnston; William H. Epstein; John P. Parise

[57] ABSTRACT

Compounds of formula I

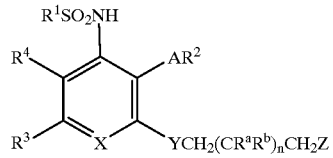

wherein $R^1$ signifies phenyl, substituted phenyl or heterocyclyl;

$R^2$ signifies phenyl or substituted phenyl;

$R^3$ signifies hydrogen, lower-alkyl, cyano, carboxy, esterified carboxy, phenyl, substituted phenyl, heterocyclyl or a residue —$CONR^5R^6$ or —$NR^5COR^7$;

$R^4$ signifies hydrogen or lower-alkyl;

$R^5$ signifies hydrogen or a residue $R^7$, and $R^6$ signifies —$(CH_2)_mR^7$; or $R^5$ and $R^6$ together with the N atom associated with them signify a heterocyclic residue;

$R^7$ signifies phenyl, substituted phenyl, cycloalkyl, heterocyclyl, lower-alkyl, cyano-lower-alkyl, hydroxylower-alkyl, di-lower-alkylamino-lower-alkyl, carboxy-lower-alkyl, lower-alkoxycarbonyl-loweralkyl, lower-alkoxycarbonylamino-lower-alkyl or phenyl-lower-alkoxycarbonyl;

$R^a$ signifies hydrogen, lower-alkyl or hydroxy;

$R^b$ signifies hydrogen or lower-alkyl;

Z signifies hydroxy, amino or a residue —$OR^8$, —$OC(O)NHR^8$, —$OC(O)OR^8$, —$NHC(O)NHR^8$ or —$NHC(O)OR^8$;

$R^8$ signifies heterocyclyl, phenyl, substituted phenyl or lower-alkyl;

A and Y each independently signify oxygen or sulphur,

X signifies nitrogen or CH;

m signifies 0, 1 or 2; and n signifies 0, 1 or 2;

and pharmaceutically usable salts thereof are inhibitors of endothelin receptors.

They can therefore be used for the treatment of disorders which are associated with endothelin activities, especially circulatory disorders such as hypertension, ischaemia, vasospasms and angina pectoris.

24 Claims, No Drawings

ARYL- AND HETARYL-SULFONAMIDE DERIVATIVES, THEIR PREPARATION AND THEIR USE AS ENDOTHELIN ANTAGONISTS

CROSS REFERENCE TO RELATED APPLICATIONS

This is a divisional of application Ser. No. 08/860,985 filed on Aug. 18, 1997, now U.S Pat. No. 5,962,687, which is a 371 of PCT/EP95/04762, filed Dec. 4, 1995.

The present invention is concerned with novel sulphonamides and their use as medicaments. In particular, the invention is concerned with novel compounds of formula I

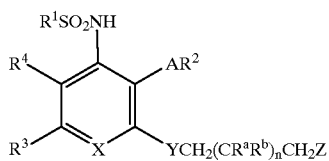

I wherein $R^1$ signifies phenyl, substituted phenyl or heterocyclyl;

$R^2$ signifies phenyl or substituted phenyl;

$R^3$ signifies hydrogen, lower-alkyl, cyano, carboxy, esterified carboxy, phenyl, substituted phenyl, heterocyclyl or a residue —$CONR^5R^6$ or —$NR^5COR^7$;

$R^4$ signifies hydrogen or lower-alkyl;

$R^5$ signifies hydrogen or a residue $R^7$, and $R^6$ signifies —$(CH_2)_m R^7$; or $R^5$ and $R^6$ together with the N atom associated with them signify a heterocyclic residue;

$R^7$ signifies phenyl, substituted phenyl, cycloalkyl, heterocyclyl, lower-alkyl, cyano-lower-alkyl, hydroxy-lower-alkyl, di-lower-alkylamino-lower-alkyl, carboxy-lower-alkyl, lower-alkoxycarbonyl-lower-alkyl, lower-alkoxycarbonylamino-lower-alkyl or phenyl-lower-alkoxycarbonyl;

$R^a$ signifies hydrogen, lower-alkyl or hydroxy;

$R^b$ signifies hydrogen or lower-alkyl;

Z signifies hydroxy, amino or a residue —$OR^8$, —$OC(O)NHR^8$, —$OC(O)OR^8$, —$NHC(O)NHR^8$ or —$NHC(O)OR^8$;

$R^8$ signifies heterocyclyl, phenyl, substituted phenyl or lower-alkyl;

A and Y each independently signify oxygen or sulphur,

X signifies nitrogen or CH;

m signifies 0, 1 or 2; and n signifies 0, 1 or 2;

and pharmaceutically usable salts thereof.

Examples of heterocyclyl residues are mono- or bicyclic 5- and 6-membered heterocyclic residues having oxygen, nitrogen or sulphur as the hetero atom, such as 2- and 3-furyl, pyrimidinyl, 2-, 3- and 4-pyridyl and pyridyl N-oxide, 5-tetrazolyl, 2-tetrazol-5-yl-4-pyridyl, 1,2- and 1,4-diazinyl, morpholino, 2- and 3-thienyl, isoxazolyl, oxazolyl, thiazolyl, imidazolyl, pyrrolyl, benzofuranyl, benzothienyl, indolyl, purinyl, quinolyl, isoquinolyl and quinazolyl, which can be substituted e.g. by lower-alkyl, lower-alkanoyl, hydroxy, lower-alkanoyloxy, lower-alkoxy, lower-alkoxycarbonyl, formyl, amino, mono- or di-lower-alkylamino or halogen. Phenyl residues can be substituted by lower-alkyl, lower alkoxy, hydroxy-lower alkyl, carboxy, lower-alkylenedioxy such as methylenedioxy or ethylenedioxy, lower-alkanoyl, hydroxy, amino, mono- or di-lower-alkylamino, phenyl and/or halogen. The term "lower" used here denotes groups with 1–7 C atoms, preferably 1–4 C atoms. Alkyl, alkoxy and alkylthio groups as well as alkyl groups as constituents of alkanoyl groups can be straight-chain or branched. Methyl, ethyl, propyl, isopropyl, butyl, sec. and tert.butyl are examples of such alkyl groups. Halogen denotes fluorine, chlorine, bromine and iodine, with chlorine being preferred. Lower-alkoxycarbonyl, aryloxycarbonyl (especially phenoxycarbonyl) and aralkoxycarbonyl (especially benzyl- and phenethyloxycarbonyl) groups are examples of esterified carboxy groups. N-Heterocyclic residues formed with $R^5$ and $R^6$ are preferably monocyclic 6-membered heterocyclyl residues which can contain a further oxygen or nitrogen atom, such as morpholino, 2,6-dimethylmorpholino, piperidino, piperazino or piperazino $N^4$-substituted by lower-alkyl, formyl or lower-alkoxycarbonyl.

Preferred residues $R^1$ are phenyl and monocyclylic heterocyclyl residues containing a nitrogen atom, such as pyridyl, especially 2-pyridyl, which can be substituted, preferably mono-substituted. Examples of preferred residues $R^1$ are especially lower-alkylphenyl, lower-alkoxyphenyl, lower-alkylthiophenyl, trifluoromethylphenyl, lower-alkylenedioxyphenyl and lower-alkylpyridyl. Preferred residues $R^2$ are phenyl substituted by lower-alkoxy and/or halogen. Preferred residues $R^3$ are hydrogen, cyano, phenyl, 5-tetrazolyl, carboxy, lower-alkoxycarbonyl and -$CONR^5R^6$, in which $R^5$ is hydrogen and $R^6$ is phenyl, phenyl substituted by lower-alkoxy, hydroxy, hydroxy-lower-alkyl, carboxy, lower-alkylenedioxy or phenyl, pyridyl, 5-tetrazolyl, lower-alkyl, cyano-lower-alkyl, hydroxy-lower-alkyl, di-lower-alkylamino-lower-alkyl, carboxy-lower-alkyl, lower-alkoxy-carbonyl-lower-alkyl, lower-alkoxycarbonylamino-lower-alkyl or phenyl-lower-alkoxycarbonyl; or $NR^5R^6$ is morpholino, 2,6-dimethylmorpholino, piperidino, piperazino, $N^4$-lower-alkylpiperazino, $N^4$-formylpiperazino or $N^4$-lower-alkoxycarbonylpiperazino. $R^4$ is preferably hydrogen. Preferred residues Z are hydroxy or, where $R^a$ is hydrogen or lower-alkyl, —$OC(O)NHR^8$ in which $R^8$ is phenyl or pyridyl. A and Y are preferably oxygen. n is preferably 0.

The compounds of formula I and their salts are inhibitors of endothelin receptors. They can therefore be used for the treatment of disorders which are associated with endothelin activities, especially circulatory disorders such as hypertension, ischaemia, vasospasms and angina pectoris.

The compounds of formula I and their salts can be manufactured in accordance with the invention by a) reacting a compound of formula II

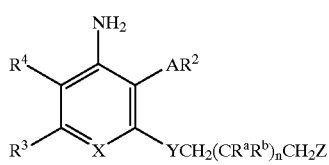

II wherein $R^2,R^3,R^4,R^a,R^b,A,X,Y,Z$ and n have the significance given above and amino or hydroxy groups optionally contained in $R^3$ and Z are present in protected form, with a reactive derivative of a sulphonic acid of the formula $R^1SO_2OH$; or b) reacting a compound of formula III

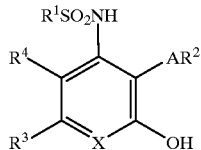

III wherein $R^1$–$R^4$, A and X have the significance given above, with a compound of the formula $HalCH_2(CR^aR^b)_nCH_2OH$, in which Hal is halogen and the hydroxy group(s) contained in the last-named compound can be present in protected form, in the presence of a base; or c) reacting a compound of formula I in which Z is hydroxy or amino and further amino or hydroxy groups which may be contained in the molecule are present in protected form, c1) with an isocyanate of the formula $R^8NCO$ or a carbamoyl chloride of the formula $R^8NCOCl$, wherein $R^8$ has the significance set forth above, or c2) with phosgene and thereafter with an alcohol of the formula $R^8OH$; or with a chloroformic acid ester of the formula $R^8OC(O)Cl$; or d) condensing a compound of formula I in which $R^3$ is carboxy with a compound of the formula $NHR^5R^6$ in which $R^5$ and $R^6$ have the significance given above; or e) reacting a compound of formula I in which $R^3$ is cyano and the remaining symbols have the significance given above with $NH_4Cl$ and sodium azide; or f) treating a compound of formula IV

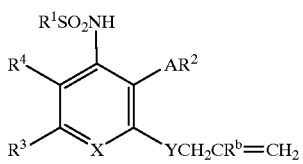

IV wherein $R^1$–$R^4$, $R^b$, A, X and Y have the significance given above, with an oxidizing agent, if desired, removing amino or hydroxy protecting groups contained in the reaction product and, if desired, transforming substituents contained in the compound of formula I obtained and/or converting the compound of formula I obtained into a salt.

As reactive derivatives of a sulphonic acid of the formula $R^1SO_2OH$ there come into consideration for the reaction with a compound of formula II e.g. halides such as chlorides. The reaction can be carried out in a manner known per se for the manufacture of sulphonamides, e.g. in an inert organic solvent such as dimethyl sulphoxide, conveniently while heating and in a protective gas atmosphere, e.g. under argon. Reactive amino or hydroxy groups present in the substituents $R^3$ and/or Z should be present in a form protected by conventional protecting groups such as tert.butoxycarbonyl or tetrahydropyranyl. The introduction of such protecting groups is conveniently effected at an earlier step in the preparation of the starting materials concerned. The cleavage of the protecting groups with the formation of a compound of formula I can be effected according to conventional procedures, e.g. by acid treatment for the cleavage of tetrahydropyranyl or tert.butoxycarbonyl groups.

In process variant b), which is preferably used for the manufacture of compounds of formula I with X=nitrogen, compounds in which Hal is iodine are conveniently used as reaction partners for compound III, Silver carbonate especially comes into consideration as the base. The reaction is conveniently carried out while heating in an inert organic solvent, e.g. in toluene while heating to about 100° C.

The reaction in accordance with process variant c) can be effected in a manner known per se for the manufacture of carbamates and ureas from alcohols and, respectively, amines. Thus, in process variant c1) a compound of formula I in which Z is hydroxy can be reacted with an isocyanate of the formula $R^8NCO$ in a suitable anhydrous organic solvent, e.g. a hydrocarbon such as toluene, conveniently while heating, to give a compound of formula I in which Z is —$OC(O)NHR^8$. The isocyanate can be generated in situ, e.g. from an azide of the formula $R^8CON_3$ by thermal decomposition. Correspondingly, compounds of formula I with Z=$NHC(O)OR^8$ can be obtained using compounds of formula I in which Z is amino.

According to process variant c2) a compound of formula I in which Z is oxygen can be converted into a compound of formula I in which Z is a residue —$OC(O)OR^8$ with phosgene and thereafter with an alcohol of the formula $R^8OH$. A phosgene salt such as diphosgene (Cl—$COOCCl_3$) or triphosgene ($CO(OCCl_3)_2$) can be used in place of phosgene. Analogously, compounds of formula I with Z=—$NHC(O)OR^8$ are obtained starting from compounds of formula I with Z=amino. The phosgene is conveniently used as a solution in an inert anhydrous organic solvent, e.g. a hydrocarbon such as toluene. The reaction with phosgene can be carried out at room temperature. The acid chloride obtained as an intermediate is reacted immediately with the alcohol $R^8OH$, conveniently while heating.

The reaction in accordance with process variant d) can be carried out in a manner known per se for the manufacture of acid amides. Conveniently, the reaction is carried out in the presence of a condensation agent such as BOP or dicyclohexylcarbodiimide in an inert organic solvent such as e.g. acetonitrile or tetrahydrofuran.

The reaction in accordance with process variant e) is carried out in a suitable solvent such as dimethylformamide, conveniently while heating, and yields compounds of formula I in which $R^3$ is 2-tetrazolyl.

Process variant f) leads to compounds of formula I in which $R^a$ and Z are hydroxy. The oxidation can be carried out e.g. using osmium tetroxide in solvents such as acetone.

Substituents present in the thus-obtained compound of formula I can be modified. For example, an ester group can be saponified to the carboxy group e.g. by treatment with aqueous alcoholic alkali. Furthermore, N-heterocyclic residues such as pyridyl can be oxidized to N-oxides. All of these reactions can be performed according to methods known per se. The compounds of formula I can be converted in a manner known per se into salts, e.g. alkali salts such as Na and K salts or alkaline earth metal salts such as Ca or Mg salts.

The compounds used as starting materials, insofar as they are not known or their preparation is described hereinafter, can be prepared in analogy to known processes or to processes described below in the Examples. Compounds of formula II in which X is CH, can be prepared starting e.g. from a 5-nitro-3,4-dihydroxy-benzoic acid ester. A reaction sequence embracing the replacement of the 4-hydroxy group by chlorine, e.g. by treatment with a chlorinating agent such as oxalyl chloride in DMF, reaction with a compound of the formula $HalCH_2(CR^aR^b)_nCH_2OR^x$, in which Hal represents halogen and $R^x$ represents a protecting group, such as tetrahydropyranyl, and further hydroxy groups present are in protected form, reaction with a phenol $R^2OH$ or a thiophenol $R^2SH$ and reduction of the nitro group to the amino group then yields a compound of formula II in which X represents CH, Y represents oxygen, Z represents a protected hydroxy group, $R^3$ represents esterified carboxy and $R^4$ represents hydrogen. An analogous procedure can be used for the preparation of corresponding compounds of formula II in which Y is sulphur. The esterified carboxy group in the thus-obtained compounds can be transformed into another residue $R^3$ in a manner known per se. Alternatively, using a suitably substituted starting material in this reaction sequence there can also be prepared corresponding compounds of formula II with $R^4$=lower-alkyl.

Compounds of formula III in which X is nitrogen can be prepared e.g. by reacting a compound of the formula $R^3$—C(NH)—$CH_2CN$ firstly with ethyl-MgBr and thereafter with a compound of the formula C(NH)—$CH_2CN$ to give a compound of the formula $R^2ACH_2COCl$. Ring-closure to a 2-hydroxy-3-$AR^{2-}$4-amino-6-$R^3$-pyridine is effected by treatment with a base such as sodium amide in dioxan. Reaction with a compound $R^1SO_2Cl$ yields a O,N-di-sulphonyl derivative from which the sulphonyloxy group can be cleaved off selectively by heating with ethanolic 1 N NaOH to 60° C. The thus-obtained compound can be converted into the desired compound of formula II with a compound of the formula $Hal-CH_2(CR^aR^b)_nCH_2OR^x$, in which $R^x$ represents a protecting group, such as tetrahydropyranyl, and further hydroxy groups present are in protected form. Conveniently, the reaction sequence described above is carried out from starting materials in which $R^3$ is a substituent, such as alkyl or phenyl, which is stable under the reaction conditions used, e.g. towards sodium amide in the cyclization, or in which an unstable or reactive substituent, such as e.g. carboxy, is present in derivatized form, e.g. as an ester, and this substituent is optionally subsequently functionally modified.

The compounds of formula I enxhibit a selective inhibitory action on endothelin receptors A and B ($ET^A$ and $ET^B$) which can be shown using the test procedures described hereinafter:

I: Inhibition of Endothelin Binding to Recombinant $ET_A$ Receptors

A cDNA coding for human $ET_A$ receptors of human placenta was cloned (M. Adachi, Y.-Y. Yang, Y. Furuichi and C. Miyamoto, BBRC 180, 1265–1272) and expressed in the baculovirus-insect cell system. Baculovirus-infected insect cells from a 23 l fermenter are centrifuged off (3000×g, 15 minutes, 4° C.) 60 hours after the infection, re-suspended in Tris buffer (5 mM, pH 7.4, 1 mM $MgCl_2$) and again centrifuged. After a further re-suspension and centrifugation the cells are suspended in 800 ml of the same buffer and freeze-dried at −120° C. The cells disintegrate when the suspension in this hypotonic buffer mixture is thawed. After a repeated freeze-drying/thawing cycle the suspension is homogenized and centrifuged (25000×g, 15 minutes, 4° C.). After suspension in Tris buffer (75 mM, pH 7.4, 25 mM $MgCl_2$, 250 mM saccharose) 1 ml aliquots (protein content about 3.5 mg/ml) are stored at −85° C.

For the binding assay, the freeze-dried membrane preparations are thawed and, after centrifugation at 20° C and 25000 g for 10 minutes, re-suspended in assay buffer (50 mM Tris buffer, pH 7.4, containing 25 mM $MnCl_2$, 1 mM EDTA and 0.5% bovine serum albumin). 100 µl of this membrane suspension containing 5 µg of protein are incubated with 50 µl of $^{125}$I-endothelin (specific activity 2200 Ci/mMol) in assay buffer (25000 cpm, final concentration 20 pM) and 100 µl of assay buffer containing varying concentrations of test compound. The incubation is carried out at 20° C. for 2 hours or at 4° C. for 24 hours. The separation of free and membrane-bound radio-ligands is carried out by filtration over a glass fibre filter.

II: Inhibition of Endothelin Binding to Human Placenta Membranes ($ET_B$ receptor) (see. Life Sci 44:1429 (1989))

Human placenta is homogenized in 5 mM Tris buffer, pH 7.4, which contains 1 mM $MgCl_2$ and 250 mM sucrose. The homogenizate is centrifuged at 4° C. and 3000 g for 15 minutes, the supernatant containing the plasma membrane fraction is centrifuged at 72000 g for 30 minutes and the precipitate is washed with 75 mM Tris buffer, pH 7.4, which contains 25 mM $MgCl_2$. Thereafter, precipitate obtained from in each case 10 g of original tissue is suspended in 1 ml of 75 mM Tris buffer, pH 7.4, containing 25 mM $MgCl_2$ and 250 mM sucrose, and freeze-dried at −20° C. in 1 ml aliquots.

For the binding assay, the freeze-dried membrane preparations are thawed and, after centrifugation at 20° C. and 25000 g for 10 minutes, re-suspended in assay buffer (50 mM Tris buffer, pH 7.4, containing 25 mM $MnCl_2$, 1 mM EDTA and 0.5% bovine serum albumin). 100 µl of this membrane suspension containing 35 µg of protein are incubated with µl of $^{125}$I-endothelin (specific activity 2200 Ci/mMol) in assay buffer (25000 cpm, final concentration 20 pM) and 100 µl of assay buffer containing varying concentrations of test compound. The incubation is carried out at 20° C. for 2 hours or at 4° C. for 24 hours. The separation of free and membrane-bound radio-ligands is carried out by filtration over a glass fibre filter.

The inhibitory activity on $ET_A$ and $ET_B$ receptors of compounds of formula I determined in these test procedures is given in Table 1 as the $IC_{50}$, i.e. as the concentration [µM] which is required to inhibit 50% of the specific binding of $^{125}$-endothelin.

TABLE 1

| Compound of Example | $ET_A$ $IC_{50}$ [µM] | $ET_B$ $IC_{50}$ [µM] |
| --- | --- | --- |
| 33 | 0.01 | 0.44 |
| 36 | 0.002 | 0.65 |
| 31 | 0.006 | 0.85 |
| 85 | 86.0 | 0.02 |
| 89 | >100 | 0.065 |
| 105 | >100 | 0.015 |

III. Inhibition of Endothelin-induced Contractions in Isolated Rat Aorta Rings

Rings with a length of 5 mm were cut out from the thorax aorta of adult Wistar-Kyoto rats. The endothelium was removed by lightly rubbing the internal surface. Each ring was immersed at 37° C. in 10 ml of Krebs-Henseleit solution in an isolated bath while gassing with 95% $O_2$ and 5% $CO_2$. The isometric stretching of the rings was measured. The rings were stretched to a pretension of 3 g. After incubation for 10 minutes with the test compound or vehicle cumulative dosages of endothelin-1 were added. The activity of the test compound was ascertained by the observed shift to the right of the dosage-activity curve of endothelin-1 in the presence of different concentrations of antagonist. This shift to the right (or "dose ratio", DR) corresponds to the quotient from the $EC_{50}$ values of endothelin-1 in the presence and in the absence of antagonist, with the $EC_{50}$ value denoting the endothelin concentration required for a half-maximum contraction.

The corresponding PA$_2$ value, which is a measure of the activity of the test compound, was calculated using a computer programme according to the following equation from the "dose ratio" DR for each individual dosage-activity curve.

pA$_2$=log(DR−1)−log(antagonist−concentration)

The EC$_{50}$ of endothelin in the absence of test compounds is 0.3 nM.

The pA$_2$ values obtained with compounds of formula I are given in Table 2.

TABLE 2

| Compound of Example | Dosage ratio (switch to the right) |
| --- | --- |
| 33 | 7.4 |
| 36 | 8.2 |

On the basis of their capability of inhibiting endothelin binding, the compounds of formula I can be used as medicaments for the treatment of disorders which are associated with vasoconstriction of increasing occurrences. Examples of such disorders are high blood pressure, especially pulmonary high pressure, and subarachnoid haemorrhage. Further indications for which the compounds in accordance with the invention can be used are coronary disorders, cardiac insufficiency, renal and myocardial ischaemia, renal insufficiency, cerebral ischaemia, cerebral infarct, migraine and Raynaud's syndrome. The compounds in accordance with the invention can also be used in atherosclerosis, the prevention of restenosis after balloon-induced vascular dilation, inflammations, gastric and duodenal ulcers, ulcus cruris, gram-negative sepsis, shock, glomerulonephtritis, renal colic, glaucoma, asthma, in dialysis and in the therapy and prophylaxis of diabetic complications and complications in the administration of cyclosporin, as well as other disorders associated with endothelin activities.

The compounds of formula I can be administered orally, rectally, parentally, e.g. intravenously, intramuscularly, subcutaneously, intrathecally or transdermally; or sublingually or as opthhalmological preparations, or as an areosol. Capsules, tablets, suspensions or solutions for oral administration, suppositories, injection solutions, eye drops, salves or spray solutions are examples of administration forms.

Intravenous, intramuscular or oral administration is a preferred form of use. The dosages in which the compounds of formula I are administered in effective amounts depend on the nature of the specific active ingredient, the age and the requirements of the patient and the mode of administration. In general, dosages of about 0.1–100 mg/kg body weight per day come into consideration. The preparations containing the compounds of formula I can contain inert or also pharmacodynamically active additives. Tablets or granulates e.g. can contain a series of binders, fillers, carriers or diluents. Liquid preparations can be present, for example, in the form of a sterile water-miscible solution. Capsules can contain a filler or thickener in addition to the active ingredient. Furthermore, flavour-improving additives as well as substances usually used as preserving, stabilizing, moisture-retaining and emulsifying agents as well as salts for varying the osmotic pressure, buffers and other additives can also be present.

The previously mentioned carrier materials and diluents can comprise organic or inorganic substances, e.g. water, gelatine, lactose, starch, magnesium stearate, talc, gum arabic, polyalkylene glycols and the like. It is a prerequisite that all adjuvants used in the production of the preparations are non-toxic.

The following Examples illustrate the invention in more detail. In the Examples RT signifies room temperature, MeOH signifies methanol and DMSO signifies dimethyl sulphoxide.

EXAMPLE 1 a) 2.08 g of methyl 3-amino-4-(2-methoxy-phenoxy)-5-[2-(tetrahydro-pyran-2-yloxy)-ethoxy]-benzoate were dissolved in pyridin (30 ml), treated dropwise while cooling with ice with a solution of 2.09 g of 4-tert-butylbenzenesulphonyl chloride in toluene (15 ml) and subsequently stirred at RT for 20 hours. The reaction mixture was partitioned between water and ethyl acetate and the organic phase was washed with 2N HCl solution and dried over magnesium sulphate. After removing the solvent methyl 3-(4-tert-butyl-benzene-sulphonylamino)-4-(2-methoxy-phenoxy)-5-[2-(tetrahydropyran-2-yloxy)-ethoxy]-benzoate was obtained as a resin.

b) A solution of 4.6 g of methyl 3-(4-tert-butyl-benzenesulphonylamino)-4-(2-methoxy-phenoxy)-5-[2-(tetrahydropyran-2-yloxy)-ethoxy]-benzoate in methanol (50 ml) was treated at RT with 4 ml of 2N aqueous HCl and the solution was subsequently stirred at RT for a further 2 hours. The solvent was removed on a rotary evaporator and the residue was partitioned between ethyl acetate and dilute potassium hydrogen carbonate solution. The organic phase was dried over magnesium sulphate, the solvent was removed on a rotary evaporator and the crude product was chromatographed over silica gel with CH$_2$Cl$_2$/ethyl acetate (5/1) as the eluent. There were thus obtained 2.57 g of methyl 3-(4-tert-butyl-phenylsulphonyl-amino)-5-(2-hydroxy-ethoxy)4-(2-methoxy-phenoxy)-benzoate as a white foam.

Preparation of the Starting Material:

c) 18.87 ml of oxalyl chloride were added dropwise to 16.95 ml of DMF at −20° C. The mixture was left to react at −20° C. for 10 minutes. Subsequently, a solution of 15.63 g of methyl 3,4-dihydroxy-5-nitro-benzoate in DMF (100 ml) was slowly added dropwise thereto, the temperature of the reaction mixture being held at 30 between −100° C. and −20° C. The mixture was left to come to room temperature and was subsequently heated for a further 5 hours on an oil bath at 100° C. (bath temperature). The dark reaction solution was poured on to ice-water, extracted at RT with ethyl acetate and the organic phase was washed three times with water, dried over sodium sulphate and concentrated on a rotary evaporator. There was thus obtained methyl 4-chloro-3-hydroxy-5-nitro-benzoate as a yellow solid which was used in the next step without further purification.

d) 6.84 g of methyl 4-chloro-3-hydroxy-5-nitro-benzoate were dissolved in acetone (150 ml), treated at RT in succession with 10.19 g of potassium carbonate and 11.19 g of 2-(2-iodo-ethoxy)-tetrahydro-pyran and the mixture was heated at reflux for 16 hours. Subsequently, the mixture was poured into water, extracted with ethyl acetate, the organic phase was dried over sodium sulphate and concentrated on a rotary evaporator. The residue was flash chromatographed on silica gel with hexane/ether (2/1) as the eluent. There was thus obtained the desired methyl 4-chloro-3-nitro-5-[2-(tetrahydro-pyran-2-yloxy)-ethoxy]-benzoate as as a pale yellow solid.

e) 4.28 g of methyl 4-chloro-3-nitro-5-[2-(tetrahydro-pyran-2-yloxy)-ethoxy]-benzoate were dissolved in acetone (250 ml), treated at RT with 5.0 g of potassium carbonate, 1.93 of guaiacol and the mixture was heated at reflux for 20 hours. It was poured on to ice-water and extracted with ethyl acetate. The organic phase was washed 3 times with 5% sodium hydroxide solution, then with water, dried over sodium sulphate and finally concentrated on a rotary evaporator. The crude product (6 g) was flash chromatographed on silica gel with hexane/ether (1/1). There was thus obtained the desired methyl 4-(2-methoxy-phenoxy)-3-nitro-5-[2-(tetrahydro-pyran-2-yloxy)-ethoxy]-benzoate as a pale yellow powder.

f) 4.3 g of methyl 4-(2-methoxy-phenoxy)-3-nitro-5-[2-(tetrahydro-pyran-2-yloxy)-ethoxy]-benzoate were dissolved in ethanol (250 ml), treated with 0.75 g of Ra-Ni catalyst and hydrogenated at RT for 3.5 hours. The catalyst was filtered off and the solution was concentrated on a rotary evaporator. There was thus obtained methyl 3-amino-4-(2-methoxy-phen-oxy)-5-[2-(tetrahydro-pyran-2-yloxy)-ethoxy]-benzoate, pale yellow solid.

EXAMPLE 2

2.57 g of methyl 3-(4-tert-butyl-phenylsulphonylamino)-5-(2-hydroxy-ethoxy)-4-(2-methoxy-phenoxy)-benzoate were dissolved in methanol (50 ml), treated with 19.4 ml of 1 M NaOH solution and subsequently heated at 65° C. for 2 hours. The mixture was poured on to ice-water, acidified with dilute HCl solution (pH 1) and the product was extracted with ethyl acetate. The organic phase was dried over sodium sulphate, concentrated and the solid obtained was dried in a high vacuum. There was thus obtained 3-(4-tert-butyl-benzenesulphonylamino)-5-(2-hydroxy-ethoxy)-4-(2-methoxy-phenoxy)-benzoic acid as a white foam.

EXAMPLE 3

77 mg of 3-(4-tert-butyl-benzenesulphonylamino)-5-(2-hydroxy-ethoxy)-4-(2-methoxy-phenoxy)-benzoic acid were dissolved in acetonitrile (5 ml), 28 μL of n-ethyldiisopropylamine, 73 mg of benzotriazol-1-yl-oxytris(dimethylamino)phosphonium hexafluorophosphate and 14 μl of morpholine were added thereto in succession and the mixture was subsequently stirred at RT for 2.5 hours. The mixture was partitioned between ethyl acetate and water, the organic phase was dried over sodium sulphate, concentrated on a rotary evaporator and the residue was chromatographed over silica gel with $CH_2Cl_2$/MeOH (20/1) as the eluent. There was thus obtained 4-tert-butyl-N-[3-(2-hydroxy-ethoxy)-2-(2-methoxy-phenoxy)-5-(morpholine-4-carbonyl)-phenyl]-benzenesulphonamide as a white foam.

EXAMPLE 4

In analogy to Example 3, from 3-(4-tert-butyl-benzenesulphonylamino)-5-(2-hydroxy-ethoxy)-4-(2-methoxy-phenoxy)-benzoic acid and piperidine there was obtained 4-tert-butyl-N-[3-(2-hydroxy-ethoxy)-2-(2-methoxy-phenoxy)-5-(piperidine-1-carbonyl)-phenyl]-benzenesulphonamide.

EXAMPLE 5

In analogy to Example 3, from 3-(4-tert-butyl-benzenesulphonylamino)-5-(2-hydroxy-ethoxy)-4-(2-methoxy-phenoxy)-benzoic acid and 2-pyridin-2-yl-ethylamine there was obtained 3-(4-tert-butyl-benzenesulphonylamino)-5-(2-hydroxy-ethoxy)-4-(2-ethoxy-phenoxy)-N-(2-pyridin-2-yl-ethyl)-benzamide.

EXAMPLE 6

In analogy to Example 3, from 3-(4-tert-butyl-benzenesulphonylamino)-5-(2-hydroxy-ethoxy)-4-(2-methoxy-phenoxy)-benzoic acid and benzyl aminoacetate there was obtained benzyl [3-(4-tert-butyl-benzenesulphonylamino)-5-(2-hydroxy-ethoxy)-4-(2-methoxy-phenoxy)-benzoylamino]-acetate.

EXAMPLE 7

In analogy to Example 3, from 3-(4-tert-butyl-benzenesulphonylamino)-5-(2-hydroxy-ethoxy)-4-(2-methoxy-phenoxy)-benzoic acid and aniline there was obtained 3-(4-tert-butyl-benzenesulphonylamino)-5-(2-hydroxy-ethoxy)-4-(2-methoxy-phenoxy)-N-phenyl-benzamide.

MS: 589.4 (M–H).

EXAMPLE 8

In analogy to Example 3, from 3-(4-tert-butyl-benzenesulphonylamino)-5-(2-hydroxy-ethoxy)-4-(2-methoxy-phenoxy)-benzoic acid and aminoacetonitrile there was obtained 3-(4-tert-butyl-benzenesulphonylamino)-N-cyanomethyl-5-(2-hydroxy-ethoxy)-4-(2-methoxy-phenoxy)-benzamide.

EXAMPLE 9

In analogy to Example 3, from 3-(4-tert-butyl-benzenesulphonylamino)-5-(2-hydroxy-ethoxy)-4-(2-methoxy-phenoxy)-benzoic acid and 2-dimethylaminoethylamine there was obtained 3-(4-tert-butyl-benzenesulphonylamino)-N-(2-dimethylamino-ethyl)-5-(2-hydroxy-ethoxy)-4-(2-methoxy-phenoxy)-benzamide.

EXAMPLE 10

In analogy to Example 3, from 3-(4-tert-butyl-benzenesulphonylamino)-5-(2-hydroxy-ethoxy)-4-(2-methoxy-phenoxy)-benzoic acid and tert-butyl (2-aminoethyl)-carbamate there was obtained tert-butyl {2-[3-(4-tert-butyl-benzenesulphonylamino)-5-(2-hydroxy-ethoxy)-4-(2-methoxy-phenoxy)-benzoylamino]-ethyl}-carbamate.

EXAMPLE 11

In analogy to Example 3, from 3-(4-tert-butyl-benzenesulphonylamino)-5-(2-hydroxy-ethoxy)-4-(2-methoxy-phenoxy)-benzoic acid and 3-picolylamine there was obtained 3-(4-tert-butyl-benzenesulphonylamino)-5-(2-hydroxy-ethoxy)-4-(2-methoxy-phenoxy)-N-pyridin-3-ylmethyl-benzamide.

EXAMPLE 12

In analogy to Example 3, from 3-(4-tert-butyl-benzenesulphonylamino)-5-(2-hydroxy-ethoxy)-4-(2-methoxy-phenoxy)-benzoic acid and benzylamine there was obtained N-benzyl-3-(4-tert-butyl-benzenesulphonylamino)-5-(2-hydroxy-ethoxy)-4-(2-methoxy-phenoxy)-benzamide.

EXAMPLE 13

By basic saponification of benzyl [3-(4-tert-butyl-benzenesulphonylamino)-5-(2-hydroxy-ethoxy)-4-(2-methoxy-phenoxy)-benzoylamino]-acetate there was obtained [3-(4-tert-butyl-benzene-sulphonylamino)-5-(2-hydroxy-ethoxy)-4-(2-methoxy-phenoxy)-benzoylamino]-acetic acid.

EXAMPLE 14

A solution of 75 mg of 4-tert-butyl-N-[3-(2-hydroxy-ethoxy)-2-(2-methoxy-phenoxy)-5-(morpholine-4- carbonyl)-phenyl]-benzenesulphonamide, 40 mg of 2-pyridylcarboxylic acid azide and 7 mg of p-dimethylaminopyridine in toluene (5 ml) was heated at 80° C. for 2 hours. The toluene was removed on a rotary evaporator and the residue was partitioned between ethyl acetate and 1N HCl solution. The organic phase was dried over magnesium sulphate and the solvent was finally removed on a rotary evaporator. The crude product was chromatographed over silica gel with CH$_2$Cl$_2$/ethyl acetate/ MeOH (60/60/3) as the eluent. There was thus obtained pyridin-2-yl-carbamic acid 2-[3-(4-tert-butyl-benzenesulphonylamino)-2-(2-methoxy-phenoxy)-5-(morpholine-4-carbonyl)-phenoxy]-ethyl ester.

White solid, 55 mg.

EXAMPLE 15

In analogy to Example 14, from 3-(4-tert-butyl-benzenesulphonylamino)-5-(2-hydroxy-ethoxy)-4-(2-methoxy-phenoxy)-N-(2-pyridin-2-yl-ethyl)-benzamide and 2-pyridylcarboxylic acid azide there was obtained pyridin-2-yl-carbamic acid 2-[3-(4-tert-butyl-benzenesulphonylamino)-2-(2-methoxy-phenoxy)-5-(2-pyridin-2-ylethylcarbamoyl)-phenoxy]-ethyl ester.

EXAMPLE 16

In analogy to Example 14, from 4-tert-butyl-N-[3-(2-hydroxy-ethoxy)-2-(2-methoxy-phenoxy)-5-(piperidine-1-carbonyl)-phenyl]-benzenesulphonamide and 2-pyridylcarboxylic acid azide there was obtained pyridin-2-yl-carbamic acid 2-[3-(4-tert-butyl-benzenesulphonylamino)-2-(2-methoxy-phenoxy)-5-(piperidine-1-carbonyl)-phenoxy]-ethyl ester.

EXAMPLE 17

In analogy to Example 14, from N-benzyl-3-(4-tert-butyl-benzenesulphonylamino)-5-(2-hydroxy-ethoxy)-4-(2-methoxy-phenoxy)-benzamide and 2-pyridylcarboxylic acid azide there was obtained pyridin-2-yl-carbamic acid 2-[5-benzylcarbamoyl-3-(4-tert-butylbenzenesulphonylamino)-2-(2-methoxy-phenoxy)-phenoxy]-ethyl ester.

EXAMPLE 18

In analogy to Example 14, from benzyl [3-(4-tert-butylbenzenesulphonylamino)-5-(2-hydroxy-ethoxy)-4-(2-methoxy-phenoxy)-benzoylamino]-acetate and 2-pyridylcarboxylic acid azide there was obtained benzyl {3-(4-tert-butyl-benzenesulphonylamino)-4-(2-methoxy-phenoxy)-5-[2-(pyridin-2-ylcarbamoyloxy)-ethoxy]-benzoylamino}-acetate.

EXAMPLE 19

In analogy to Example 14, from 3-(4-tert-butyl-benzenesulphonylamino)-5-(2-hydroxy-ethoxy)-4-(2-methoxy-phenoxy)-N-pyridin-3-ylmethyl-benzamide and 2-pyridylcarboxylic acid azide there was obtained pyridin-2-yl-carbamic acid 2-{3-(4-tert-butylbenzenesulphonylamino)-2-(2-methoxy-phenoxy)-5-[(pyridin-3-ylmethyl)-carbamoyl]-phenoxy}-ethyl ester.

EXAMPLE 20

In analogy to Example 14, from 3-(4-tert-butylbenzenesulphonylamino)-5-(2-hydroxy-ethoxy)-4-(2-methoxy-phenoxy)-N-phenyl-benzamide and 2-pyridylcarboxylic acid azide there was obtained pyridin-2-yl-carbamic acid 2-[3-(4-tert-butyl-benzenesulphonylamino)-2-(2-methoxy-phenoxy)-5-phenylcarbamoyl-phenoxy]-ethyl ester.

EXAMPLE 21 a) 0.417 g of methyl 3-amino-4-(2-methoxy-phenoxy)-5-[2-(tetrahydro-pyran-2-yloxy)-ethoxy]-benzoate was dissolved in pyridine (7.5 ml), treated dropwise while cooling with ice with a solution of 0.395 g of 5-isopropylpyridine-2-sulphonyl chloride in toluene (3.5 ml) and subsequently stirred at RT for 20 hours. The reaction mixture was partitioned between water and CH$_2$Cl$_2$, the organic phase was washed with 1M HCl solution and then with 1M potassium hydrogen carbonate solution and dried over magnesium sulphate. After removing the solvent methyl 3-(5-isopropyl-pyridine- 2-sulphonylamino)-4-(2-methoxy-phenoxy)-5-[2-(tetrahydro-pyran-2-yloxy)-ethoxy]-benzoate (0.6 g) was obtained as a resin.

b) A solution of 0.6 g of methyl 3-(5-isopropyl-pyridine-2-sulphonylamino)-4-(2-methoxy-phenoxy)-5-[2-(tetrahydro-pyran-2-yloxy)-ethoxy]-benzoate in methanol (10 ml) was treated at RT with 1 ml of 2M aqueous HCl and the solution was subsequently stirred at RT for a further 1 hour. The solvent was removed on a rotary evaporator and the residue was partitioned between ethyl acetate and dilute potassium hydrogen carbonate solution. The organic phase was dried over magnesium sulphate, the solvent was removed on a rotary evaporator and the crude product was chromatographed over silica gel with CH$_2$Cl$_2$/ethyl acetate (5/1) as the eluent. There was thus obtained 0.459 g of methyl 3-(2-hydroxy-ethoxy)-5-(5-isopropyl-pyridine-2-sulphonylamino)-4-(2-methoxy-phenoxy)-benzoate as a white foam.

EXAMPLE 22

0.459 g of methyl 3-(2-hydroxy-ethoxy)-5-(5-isopropyl-pyridine-2-sulphonylamino)-4-(2-methoxy-phenoxy)-benzoate was dissolved in ethanol (10 ml), treated with 3.5 ml of 1M NaOH solution and subsequently heated at 80° C. for 1.5 hours. The mixture was poured on to ice-water, acidified with dilute HCl solution (pH 1) and the product was extracted with ethyl acetate. The organic phase was dried over sodium sulphate, concentrated and the solid obtained was dried in a high vacuum. There was thus obtained 3-(2-hydroxy-ethoxy)-5-(5-isopropyl-pyridine-2-sulphonylamino)-4-(2-methoxy-phenoxy)-benzoic acid as a white foam (0.474 g).

EXAMPLE 23

55 mg of 3-(2-hyd roxy-ethoxy)-5-(5-isopropyl-pyridine-2-sulphonylamino)-4-(2-methoxy-phenoxy)-benzoic acid were dissolved in acetonitrile (5 ml), 19 μl of n-ethyldiisopropylamine, 49 mg of benzotriazol-1-yl-oxytris (dimethylamino)phosphonium hexafluorophosphate and 10 μl of morpholine were added thereto in succession at RT and the mixture was subsequently stirred at RT for 16 hours. The mixture was partitioned between ethyl acetate and water, the organic phase was dried over sodium sulphate, concentrated on a rotary evaporator and the residue was chromatographed over silica gel with CH$_2$Cl$_2$/MeOH (20/1) as the eluent. There was thus obtained 5-isopropyl-pyridine-2-sulphonic acid [3-(2-hydroxy-ethoxy)-2-(2-methoxy-phenoxy)-5-(morpholine-4-carbonyl)-phenyl]-amide as a white foam.

EXAMPLE 24

In analogy to Example 23, from 3-(2-hydroxy-ethoxy)-5-(5-isopropyl-pyridine-2-sulphonylamino)-4-(2-methoxyphenoxy)-benzoic acid and piperidine there was obtained 5-isopropyl-pyridine-2-sulphonic acid [3-(2-hydroxy-ethoxy)-2-(2-methoxy-phenoxy)-5-(piperidine-1-carbonyl)-phenyl]-amide.

EXAMPLE 25

In analogy to Example 23, from 3-(2-hydroxy-ethoxy)-5-(5-isopropyl-pyridine-2-sulphonylamino)-4-(2-methoxy-phenoxy)-benzoic acid and 1-methylpiperazine there was obtained 5-isopropyl-pyridine-2-sulphonic acid [3-(2-hydroxy-ethoxy)-2-(2-methoxy-phenoxy)-5-(4-methyl-piperazine-1-carbonyl)-phenyl]-amide.

EXAMPLE 26

In analogy to Example 23, from 3-(2-hydroxy-ethoxy)-5-(5-isopropyl-pyridine-2-sulphonylamino)-4-(2-methoxy-phenoxy)-benzoic acid and 2,6-dimethyl-morpholine there was obtained 5-isopropyl-pyridine-2-sulphonic acid [5-(2,6-dimethyl-morpholine-4-carbonyl)-3-(2-hydroxy-ethoxy)-2-(2-methoxy-phenoxy)-phenyl]-amide.

EXAMPLE 27

In analogy to Example 23, from 3-(2-hydroxy-ethoxy)-5-(5-isopropyl-pyridine-2-sulphonylamino)-4-(2-methoxy-phenoxy)-benzoic acid and 2-pyridin-2-yl-ethylamine there was obtained 3-(2-hydroxy-ethoxy)-5-(5-isopropyl-pyridine-2-sulphonylamino)-4-(2-methoxy-phenoxy)-N-(2-pyridin-2-yl-ethyl)-benzamide.

EXAMPLE 28

In analogy to Example 23, from 3-(2-hydroxy-ethoxy)-5-(5-isopropyl-pyridine-2-sulphonylamino)-4-(2-methoxy-phenoxy)-benzoic acid and ethyl piperazine-1-carboxylate there was obtained ethyl 4-[3-(2-hydroxyethoxy)-5-(5-isopropyl-pyridine-2-sulphonylamino)-4-(2-methoxy-phenoxy)-benzoyl]-piperazine-1-carboxylate.

EXAMPLE 29

In analogy to Example 23, from 3-(2-hydroxy-ethoxy)-5-(5-isopropyl-pyridine-2-sulphonylamino)-4-(2-methoxy-phenoxy)-benzoic acid and piperazine-1-carbaldehyde there was obtained 5-isopropyl-pyridine-2-sulphonic acid [5-(4-formyl-piperazine-1-carbonyl)-3-(2-hydroxy-ethoxy)-2-(2-methoxy-phenoxy)-phenyl]-amide.

EXAMPLE 30

In analogy to Example 23, from 3-(2-hydroxy-ethoxy)-5-(5-isopropyl-pyridine-2-sulphonylamino)-4-(2-methoxy-phenoxy)-benzoic acid and propylamine there was obtained 3-(2-hydroxy-ethoxy)-5-(5-isopropyl-pyridine-2-sulphonylamino)-4-(2-methoxy-phenoxy)-N-propylbenzamide.

EXAMPLE 31

A solution of 50 mg of 5-isopropyl-pyridine-2-sulphonic acid [3-(2-hydroxy-ethoxy)-2-(2-methoxy-phenoxy)-5-(morpholine-4-carbonyl)-phenyl]-amide, 36 mg of 2-pyridylcarboxylic acid azide and 5 mg of p-dimethylaminopyridine in toluene (5 ml) was heated at 135° C. (bath temperature) for 2 hours. The residue was partitioned between ethyl acetate and 1N HCl solution, the aqueous phase was extracted several times with methylene chloride and the organic phase was dried over magnesium sulphate. The solvent was finally removed on a rotary evaporator and the crude product was chromatographed over silica gel with $CH_2Cl_2$/MeOH (20/1/) as the eluent. There was thus obtained pyridin-2-yl-carbamic acid 2-[3-(5-isopropyl-pyridine- 2-sulphonylamino)-2-(2-methoxy-phenoxy)-5(morpholine-4-carbonyl)-phenoxy]-ethyl ester.

White solid.

EXAMPLE 32

In analogy to Example 31, from 5-isopropyl-pyridine-2-sulphonic acid [3-(2-hydroxy-ethoxy)-2-(2-methoxy-phenoxy)-5-(piperidine-1-carbonyl)-phenyl]-amide and 2-pyridylcarboxylic acid azide there was obtained pyridin-2-yl-carbamic acid 2-[3-(5-isopropyl-pyridine-2-sulphonylamino)-2-(2-methoxy-phenoxy)-5-(piperidine-1-carbonyl)-phenoxy]-ethyl ester.

EXAMPLE 33

In analogy to Example 31, from 5-isopropyl-pyridine-2-sulphonic acid [3-(2-hydroxy-ethoxy)-2-(2-methoxy-phenoxy)-5-(4-methyl-piperazine-1-carbonyl)-phenyl]-amide and 2-pyridylcarboxylic acid azide there was obtained pyridin-2-yl-carbamic acid 2-[3-(5-isopropyl-pyridine-2-sulphonylamino)-2-(2-methoxy-phenoxy)-5-(4-methyl-piperazine-1-carbonyl)-phenoxy]-ethyl ester.

EXAMPLE 34

In analogy to Example 31, from 5-isopropyl-pyridine-2-sulphonic acid [5-(2,6-dimethyl-morpholine-4-carbonyl)-3-(2-hydroxy-ethoxy)-2-(2-methoxy-phenoxy)-phenyl]-amide and 2-pyridylcarboxylic acid azide there was obtained pyridin-2-yl-carbamic acid 2-[5-(2,6-dimethyl-morpholine-4-carbonyl)-3-(5-isopropyl-pyridine-2-sulphonylamino)-2-(2-methoxy-phenoxy)-phenoxy]-ethyl ester.

EXAMPLE 35

In analogy to Example 31, from 3-(2-hydroxy-ethoxy)-5-(5-isopropyl-pyridine-2-sulphonylamino)-4-(2-methoxy-phenoxy)-N-(2-pyridin-2-yl-ethyl)-benzamide and 2-pyridylcarboxylic acid azide there was obtained pyridin-2-yl-carbamic acid 2-[3-(5-isopropyl-pyridine-2-sulphonylamino)-2-(2-methoxy-phenoxy)-5-(2-pyridin-2-ylethylcarbamoyl)-phenoxy]-ethyl ester.

EXAMPLE 36

In analogy to Example 31, from ethyl 4-[3-(2-hydroxy-ethoxy)-5-(5-isopropyl-pyridine-2-sulphonylamino)-4-(2-methoxy-phenoxy)-benzoyl]-piperazine-1-carboxylate and 2-pyridylcarboxylic acid azide there was obtained ethyl 4-{3-(5-isopropyl-pyridine-2-sulphonylamino)-4-(2-methoxy-phenoxy)-5-[2-(pyridin-2-ylcarbamoyloxy)-ethoxy]-benzoyl}-piperazine-1-carboxylate.

EXAMPLE 37

In analogy to Example 31, from 5-isopropyl-pyridine-2-sulphonic acid [5-(4-formyl-piperazine-1-carbonyl)-3-(2-hydroxy-ethoxy)-2-(2-methoxy-phenoxy)-phenyl]-amide and 2-pyridylcarboxylic acid azide there was obtained pyridin-2-yl-carbamic acid 2-[5-(4-formyl-piperazine-1-carbonyl)-3-(5-isopropyl-pyridine-2-sulphonylamino)-2-(2-methoxy-phenoxy)-phenoxy]-ethyl ester.

EXAMPLE 38 a) 1.04 g of methyl 3-amino-4-(2-methoxy-phenoxy)-5-[2-(tetrahydro-pyran-2-yloxy)-ethoxy]-benzoate were dissolved in pyridine (30 ml), treated dropwise while cooling with ice with a solution of 1.1 g of benzo[1,3]-dioxol-5-sulphonyl chloride in toluene (10 ml) and subsequently stirred at RT for 20 hours. The reaction mixture was poured on to ice/3M HCl, the product was extracted with ethyl acetate and the organic phase was dried over magnesium sulphate. After removing the solvent there was obtained the desired methyl 3-(benzo[1,3]dioxol-5-sulphonylamino)-4-(2-methoxy-phenoxy)-5-[2-(tetrahydro-pyran-2-yloxy)-ethoxy]-benzoate as a resin.

b) A solution of 1.5 g of methyl 3-(benzo[1,3]dioxol-5-sulphonylamino)-4-(2-methoxy-phenoxy)-5-[2-(tetrahydro-pyran-2-yloxy)-ethoxy]-benzoate in methanol (50 ml) was treated at RT with 3 ml of 5M aqueous HCl and the solution was subsequently stirred at RT for a further 2.5 hours. The solvent was removed on a rotary evaporator and the residue was taken up in ethyl acetate and washed with 2N potassium hydrogen carbonate solution. The organic phase was dried over magnesium sulphate, the solvent was removed on a rotary evaporator and the crude product (1.7 g) was chromatographed over silica gel with $CH_2Cl_2$/ethyl acetate (8/1) as the eluent. There was thus obtained methyl 3-(benzo[1,3]dioxol-5sulphonylamino)-5-(2-hydroxy-ethoxy)-4-(2-methoxy-phenoxy)-benzoate as a white solid.

EXAMPLE 39

1.17 g of methyl 3-(benzo[1,3]dioxol-5-sulphonylamino)-5-(2-hydroxy-ethoxy)-4-(2-methoxy-phenoxy)-benzoate were dissolved in methanol (20 ml), treated with 9 ml of 1M NaOH solution and subsequently heated at reflux for 3 hours. The mixture was poured on to ice-water, acidified with dilute HCl solution, pH 1, and the product was extracted with ethyl acetate. The organic phase was dried over sodium sulphate, concentrated and the solid obtained was dried in a high vacuum. There was thus obtained 3-(benzo[1,3]dioxol-5-sulphonylamino)-5-(2-hydroxy-ethoxy)-4-(2-methoxy-phenoxy)-benzoic acid as a white foam.

EXAMPLE 40

50 mg of 3-(benzo[1,3]dioxol-5-sulphonylamino)-5-(2-hydroxy-ethoxy)-4-(2-methoxy-phenoxy)-benzoic acid were dissolved in acetonitrile (5 ml), 19 μl of n-ethyldiisopropylamine, 49 mg of benzotriazol-1-yl-oxytris(dimethylamino)phosphonium hexafluorophosphate and 10 μl of morpholine were added in succession at RT and the mixture was subsequently stirred at RT for 3 hours. The mixture was partitioned between ethyl acetate and water, the organic phase was dried over sodium sulphate, concentrated on a rotary evaporator and the residue was chromatographed over silica gel with $CH_2Cl_2$/MeOH (20/1) as the eluent. There was thus obtained benzo[1,3]dioxol-5-sulphonic acid [3-(2-hydroxy-ethoxy)-2-(2-methoxy-phenoxy)-5-(morpholine-4-carbonyl)-phenyl]-amide as a white foam.

EXAMPLE 41

In analogy to Example 40, from 3-(benzo[1,3]dioxol-5-sulphonylamino)-5-(2-hydroxy-ethoxy)-4-(2-methoxy-phenoxy)-benzoic acid and 1-ethoxycarbonylpiperazine there was obtained ethyl N4-[3-benzo[1,3]dioxol-5-sulphonylamino)-5-(2-hydroxy-ethoxy)-4-(2-methoxy-phenoxy)-benzoyl]-piperazine-1-carboxylate.

EXAMPLE 42

In analogy to Example 40, from 3-(benzo[1,3]dioxol-5-sulphonylamino)-5-(2-hydroxy-ethoxy)-4-(2-methoxy-phenoxy)-benzoic acid and isobutylamine there was obtained 3-(benzo[1,3]dioxol-5-sulphonylamino)-5-(2-hydroxy-ethoxy)-N-isobutyl-4-(2-methoxy-phenoxy)-benzamide.

EXAMPLE 43

In analogy to Example 40, from 3-(benzo[1,3]dioxol-5-sulphonylamino)-5-(2-hydroxy-ethoxy)-4-(2-methoxy-phenoxy)-benzoic acid and isopropylamine there was obtained 3-(benzo[1,3]dioxol-5-sulphonylamino)-5-(2-hydroxy-ethoxy)-N-isopropyl-4-(2-methoxy-phenoxy)-benzamide.

EXAMPLE 44

In analogy to Example 40, from 3-(benzo[1,3]dioxol-5-sulphonylamino)-5-(2-hydroxy-ethoxy)-4-(2-methoxy-phenoxy)-benzoic acid and ethanolamine there was obtained 3-(benzo[1,3]dioxol-5-sulphonylamino)-5-(2-hydroxy-ethoxy)-N-(2-hydroxy-ethyl)-4-(2-methoxy-phenoxy)-benzamide.

EXAMPLE 45

A solution of 52 mg of methyl 3-(benzo[1,3]dioxol-5-sulphonylamino)-4-(2-methoxy-phenoxy)-5-[2-(tetrahydro-pyran-2-yloxy)-ethoxy]-benzoate, 44 mg of 2-pyridylcarboxylic acid azide and 5 mg of p-dimethylaminopyridine in toluene (5 ml) was heated at 110° C. (bath temperature) for 1.5 hours. The residue was partitioned between ethyl acetate and 1N HCl solution, the aqueous phase was extracted several times with methylene chloride and the organic phase was dried over magnesium sulphate. The solvent was finally removed on a rotary evaporator and the crude product was chromatographed over silica gel with $CH_2Cl_2$/ethyl acetate (210/1) as the eluent. There was thus obtained methyl 3-(benzo[1,3]dioxol-5-sulphonylamino)-4-(2-methoxy-phenoxy)-5-[2-(pyridin-2-ylcarbamoyloxy)-ethoxy]-benzoate as a white solid.

EXAMPLE 46

In analogy to Example 45, from benzo[1,3]dioxol-5-sulphonic acid [3-(2-hydroxy-ethoxy)-2-(2-methoxy-phenoxy)-5-(morpholine-4-carbonyl)-phenyl]-amide and 2-pyridylcarboxylic acid azide there was obtained pyridin-2-yl-carbamic acid 2-[3-(benzo[1,3]dioxol-5-sulphonylamino)-2-(2-methoxy-phenoxy)-5-(morpholine-4-carbonyl)-phenoxy]-ethyl ester.

EXAMPLE 47

In analogy to Example 45, from ethyl 4-[3-(benzo[1,3]dioxol-5-sulphonylamino)-5-(2-hydroxy-ethoxy)-4-(2-methoxy-phenoxy)-benzoyl]-piperazine-1-carboxylate and 2-pyridylcarboxylic acid azide there was obtained ethyl 4-{3-(benzo[1,3]dioxol-5-sulphonylamino)-4-(2-methoxy-phenoxy)-5-[2-(pyridin-2-ylcarbamoyloxy)-ethoxy]-benzoyl}-piperazine-1-carboxylate.

EXAMPLE 48

In analogy to Example 45, from 3-(benzo[1,3]dioxol-5-sulphonylamino)-5-(2-hydroxy-ethoxy)-N-isobutyl-4-(2-methoxy-phenoxy)-benzamide and 2-pyridylcarboxylic acid azide there was obtained pyridin-2-yl-carbamic acid 2-[3-(benzo[1,3]dioxol-5-sulphonylamino)-5-isobutylcarbamoyl-2-(2-methoxy-phenoxy)-phenoxy]-ethyl ester.

EXAMPLE 49

In analogy to Example 45, from 3-(benzo[1,3]dioxol-5-sulphonylamino)-5-(2-hydroxy-ethoxy)-N-isopropyl-4-(2-methoxy-phenoxy)-benzamide and 2-pyridylcarboxylic acid azide there was obtained pyridin-2-yl-carbamic acid 2-[3-(benzo[1,3]dioxol-5-sulphonylamino)-5-isopropylcarbamoyl-2-(2-methoxy-phenoxy)-phenoxy]-ethyl ester.

EXAMPLE 50 a) 2.14 g of methyl 3-amino-4-(2-methoxy-phenoxy)-5-[2-(tetrahydro-pyran-2-yloxy)-ethoxy]-benzoate were dissolved in in pyridine (30 ml), treated dropwise while cooling with ice with a solution of 1.488 g of 4-methoxybenzenesulphonyl chloride in toluene (10 ml) and subsequently stirred at RT for 20 hours. The reaction mixture was poured on to ice/3M HCl, the product was extracted with ethyl acetate and the organic phase was dried over magnesium sulphate. After removing the solvent there was obtained methyl 3-(4-methoxy-benzenesulphonylamino)-4-(2-methoxy-phenoxy)-5-[2-(tetrahydro-pyran-2-yloxy)-ethoxy]-benzoate as a resin.

b) A solution of 2.17 g of methyl 3-(4-methoxy-benzenesulphonylamino)-4-(2-methoxy-phenoxy)-5-[2-(tetrahydro-pyran-2-yloxy)-ethoxy]-benzoate in methanol (10 ml) was treated at RT with 10 ml of 5.5M aqueous HCl and the solution was subsequently stirred at RT for a further 5 hours. The solvent was removed on a rotary evaporator and the residue was taken up in ethyl acetate and washed with 2N potassium hydrogen carbonate solution. The organic phase was dried over magnesium sulphate, the solvent was removed on a rotary evaporator and the crude product was chromatographed over silica gel with $CH_2Cl_2$/ethyl acetate (10/1) as the eluent. There was thus obtained methyl 3-(2-hydroxy-ethoxy)-5-(4-methoxybenzenesulphonylamino)-4-(2-methoxy-phenoxy)-benzoate as a white solid.

b) A solution of 2.17 g of methyl 3-(4-methoxy-benzenesulphonylamino)-4-(2-methoxy-phenoxy)-5-[2-(tetrahydro-pyran-2-yloxy)-ethoxy]-benzoate in methanol (10 ml) was treated at RT with 10 ml of 5.5M aqueous HCl and the solution was subsequently stirred at RT for a further 5 hours. The solvent was removed on a rotary evaporator, the residue was taken up in ethyl acetate and washed with 2N potassium hydrogen carbonate solution. The organic phase was dried over magnesium sulphate, the solvent was removed on a rotary evaporator and the crude product was chromatographed over silica gel with $CH_2Cl_2$/ethyl acetate (10/1) as the eluent. There was thus obtained methyl 3-(2-hydroxy-ethoxy)-5-(4-methoxybenzenesulphonylamino)-4-(2-methoxy-phenoxy)-benzoate as a white solid.

EXAMPLE 51

0.88 g of methyl 3-(4-methoxy-benzenesulphonylamino)-4-(2-methoxy-phenoxy)-5-[2-(tetrahydro-pyran-2-yloxy)-ethoxy]-benzoate was dissolved in methanol (10 ml), treated with 7 ml of 1M NaOH solution and subsequently heated at reflux for 1.5 hours. The mixture was poured on to ice-water, acidified with dilute HCl solution, pH 1, and the product was extracted with ethyl acetate. The organic phase was dried over sodium sulphate, concentrated and the solid obtained was dried in a high vacuum. There was thus obtained 3-(2-hydroxy-ethoxy)-5-(4-methoxy-benzenesulphonylamino)-4-(2-methoxy-phenoxy)-benzoic acid as a white foam (0.75 g).

EXAMPLE 52

49 mg of 3-(2-hydroxy-ethoxy)-5-(4-methoxy-benzenesulphonyl-amino)-4-(2-methoxy-phenoxy)-benzoic acid were dissolved in acetonitrile (5 ml), 19 pl of n-ethyldiisopropylamine, 49 mg of benzotriazol-1-yl-oxytris (dimethylamino)-phosphonium hexafluorophosphate and 10 µl of morpholine were added in succession at RT and the mixture was subsequently stirred at RT for 12 hours. The mixture was partitioned between ethyl acetate and water, the organic phase was dried over sodium sulphate, concentrated on a rotary evaporator and the residue was chromatographed over silica gel with $CH_2Cl_2$/MeOH (30/1) as the eluent. There was thus obtained N-[3-(2-hydroxy-ethoxy)-2-(2-methoxy-phenoxy)-5-(morpholine-4-carbonyl)-phenyl]-4-methoxy-benzenesulphonamide as a white foam.

EXAMPLE 53

A solution of 50 mg of methyl 3-(2-hydroxy-ethoxy)-5-(4-methoxy-benzenesulphonylamino)-4-(2-methoxy-phenoxy)-benzoate, 45 mg of 2-pyridylcarboxylic acid azide and 5 mg of p-dimethylaminopyridine in toluene (5 ml) was heated at 110° C. (bath temperature) for 1 hour. The residue was partitioned between ethyl acetate and 1N HCl solution, the aqueous phase was extracted several times with methylene chloride and the organic phase was dried over magnesium sulphate. The solvent was finally removed on a rotary evaporator and the crude product was chromatographed over silica gel with $CH_2Cl_2$/ethyl acetate (20I/) as the eluent. There was thus obtained methyl 3-(4-methoxy-benzenesulphonylamino)-4-(2-methoxy-phenoxy)-5-[2-(pyridin-2-ylcarb-amoyloxy)-ethoxy]-benzoate.

White solid.

EXAMPLE 54

In analogy to Example 53, from N-[3-(2-hydroxy-ethoxy)-2-(2-methoxy-phenoxy)-5-(morpholine-4-carbonyl)-phenyl]-4-methoxy-benzenesulphonamide and 2-pyridylcarboxylic acid azide there was obtained pyridin-2-yl-carbamic acid 2-[3-(4-methoxy-benzenesulphonylamino)-2-(2-methoxy-phenoxy)-5-(morpholine-4-carbonyl)-phenoxy]-ethyl ester.

EXAMPLE 55 a) 0.626 g of methyl 3-amino-4-(2-methoxy-phenoxy)-5-[2-(tetrahydro-pyran-2-yloxy)-ethoxy]-benzoate was dissolved in pyridine (30 ml), treated dropwise while cooling with ice with a solution of 0.593 g of 4-methylsulphanylbenzenesulphonyl chloride in toluene (10 ml) and subsequently stirred at RT for 20 hours. The reaction mixture was poured on to ice/3M HCl, the product was extracted with ethyl acetate and the organic phase was dried over magnesium sulphate. After removing the solvent there was obtained methyl 4-(2-methoxy-phenoxy)-3-(4-methylsulphanyl-benzenesulphonylamino)-5-[2-(tetrahydro-pyran-2-yloxy)-ethoxy]-benzoate as a yellow oil.

b) A solution of 0.91 g of methyl 4-(2-methoxy-phenoxy)-3-(4-methylsulphanyl-benzenesulphonylamino)-5-[2-(tetrahydro-pyran-2-yloxy)-ethoxy]-benzoate in methanol (30 ml) was treated at 0° C. with 5 ml of 5.5M aqueous HCl and the solution was subsequently stirred at 0° C. for a further 1 hour The solvent was removed on a rotary evaporator and the residue was taken up in ethyl acetate and washed with 2N potassium hydrogen carbonate solution. The organic phase was dried over magnesium sulphate, the solvent was removed on a rotary evaporator and the crude product was chromatographed over silica gel with $CH_2Cl_2$/ethyl acetate (7/1) as the eluent. There was thus obtained methyl 3-(2-hydroxy-ethoxy)-4-(2-methoxy-phenoxy)-5-(4-methylsulphanyl-benzenesulphonylamino)-benzoate as a white foam.

EXAMPLE 56

0.78 g of methyl 3-(2-hydroxy-ethoxy)-4-(2-methoxy-phenoxy)-5-(4-methylsulphanyl-benzenesulphonylamino)-benzoate was dissolved in methanol (30 ml), treated with 9 ml of 1M NaOH solution and subsequently heated at reflux for 1.5 hours. The 30 mixture was poured on to ice-water, acidified with dilute HCl solution (pH 1) and the product was extracted with ethyl acetate. The organic phase was dried over sodium sulphate, concentrated and the solid obtained was dried in a high vacuum. There was thus obtained 3-(2-hydroxy-ethoxy)-4-(2-methoxy-phenoxy)-5-(4-methylsulphanyl-benzenesulphonylamino)-benzoic acid as a white foam (0.79 g).

EXAMPLE 57

75 mg of 3-(2-hydroxy-ethoxy)-4-(2-methoxy-phenoxy)-5-(4-methylsulphanyl-benzenesulphonylamino)-benzoic acid were dissolved in acetonitrile (15 ml), 29 , n-ethyldiisopropylamine, 75 mg of benzotriazol-1-yl-oxytris(dimethylamino)-phosphonium hexafluorophosphate and 14 µl of morpholine were added in succession at RT and the mixture was subsequently stirred at room temperature for 20 hours. The mixture was partitioned between ethyl acetate and water, the organic phase was dried over sodium sulphate, concentrated on a rotary evaporator and the residue was chromatographed over silica gel with $CH_2Cl_2$/MeOH (20/1) as the eluent. There was thus obtained N-[3-(2-hydroxy-ethoxy)-2-(2-methoxy-phenoxy)-5-(morpholine-4-carbonyl)-phenyl]-4-methylsulphanyl-benzenesulphonamide (71 mg) as a white foam.

EXAMPLE 58

In analogy to Example 57, from 3-(2-hydroxy-ethoxy)-4-(2-methoxy-phenoxy)-5-(4-methylsulphanyl-benzenesulphonylamino)-benzoic acid and 1-ethoxycarbonylpiperazine there was obtained ethyl 4-[3-(2-hydroxy-ethoxy)-4-(2-methoxy-phenoxy)-5-(4-methylsulphanyl-benzenesulphonyl-amino)-benzoyl]-piperazine-1-carboxylate.

EXAMPLE 59

A solution of 63 mg of N-[3-(2-hydroxy-ethoxy)-2-(2-methoxy-phenoxy)-5-(morpholine-4-carbonyl)-phenyl]-4-methylsulphanyl-benzenesulphonamide, 48 mg of 2-pyridylcarboxylic acid azide and 5 mg of p-dimethylaminopyridine in toluene (15 ml) was heated at 110° C. (bath temperature) for 2 hours. The residue was partitioned between methylene chloride and 1N HCl solution, the aqueous phase was extracted several times with methylene chloride and the organic phase was dried over magnesium sulphate. The solvent was finally removed on a rotary evaporator and the crude product was chromatographed over silica gel with $CH_2Cl_2$/MeOH (30/1/) as the eluent. There was thus obtained pyridin-2-yl-carbamic acid 2-[2-(2-methoxy-phenoxy)-3-(4-methylsulphanyl-benzenesulphonylamino)-5-(morpholine-4-carbonyl)-phenoxy]-ethyl ester as a white solid,

EXAMPLE 60

In analogy to Example 59, from ethyl 4-[3-(2-hydroxy-ethoxy)-4-(2-methoxy-phenoxy)-5-(4-methylsulphanyl-benzenesulphonylamino)-benzoyl]-piperazine-1-carboxylate and 2-pyridylcarboxylic acid azide there was obtained ethyl 4-{4-(2-methoxy-phenoxy)-3-(4-methylsulphanylbenzenesulphonylamino)-5-[2-(pyridin-2-ylcarbamoyloxy)-ethoxy]-benzoyl}-piperazine-1-carboxylate.

EXAMPLE 61 a) 1.04 g of methyl 3-amino-4-(2-methoxy-phenoxy)-5-[2-(tetrahydro-pyran-2-yloxy)-ethoxy]-benzoate were dissolved in pyridine (30 ml), treated dropwise while cooling with ice with a solution of 0.953 g of 4-methyl-benzenesulphonyl chloride in toluene (10 ml) and subsequently stirred at RT for 20 hours. The reaction mixture was poured on to ice/3M HCl, the product was extracted with ethyl acetate and the organic phase was dried over magnesium sulphate. After removing the solvent there was obtained methyl 4-(2-methoxy-phenoxy)-3-[2-(tetrahydro-pyran-2-yloxy)-ethoxy]-5-(toluene-4-sulphonylamino)-benzoate as a yellow solid.

b) A solution of 1.42 g of methyl 4-(2-methoxy-phenoxy)-3-[2-(tetrahydro-pyran-2-yloxy)-ethoxy]-5-(toluene-4-sulphonylamino)-benzoate in methanol (50 ml) was treated at RT with 3 ml of 5.5M aqueous HCl and the solution was subsequently stirred at RT for a further 5 hours. The solvent was removed on a rotary evaporator and the residue was taken up in ethyl acetate and washed with 2N potassium hydrogen carbonate solution. The organic phase was dried over magnesium sulphate, the solvent was removed on a rotary evaporator and the crude product was chromatographed over silica gel with $CH_2Cl_2$/ethyl acetate (9/1) as the eluent. There were thus obtained 1.15 g of methyl 3-(2-hydroxy-ethoxy)-4-(2-methoxy-phenoxy)-5-(toluene-4-sulphonylamino)-benzoate as a white foam.

EXAMPLE 62

1.069 g of methyl 3-(2-hydroxy-ethoxy)-4-(2-methoxy-phenoxy)-5-(toluene-4-sulphonylamino)-benzoate were dissolved in methanol (50 ml), treated with 11 ml of 1M NaOH solution and subsequently heated at reflux for 20 hours. The mixture was poured on to ice-water, acidified with dilute HCl solution (pH 1) and the product was extracted with ethyl acetate. The organic phase was dried over sodium sulphate, concentrated and the solid obtained was dried in a high vacuum. There was thus obtained 3-(2-hydroxy-ethoxy)-4-(2-methoxy-phenoxy)-5-(toluene-4-sulphonylamino)-benzoic acid as a white foam.

EXAMPLE 63

70 mg of 3-(2-hydroxy-ethoxy)-4-(2-methoxy-phenoxy)-5-(toluene-4-sulphonylamino)-benzoic acid were dissolved in acetonitrile (5 ml), 29 µl of n-ethyldiisopropylamine, 75 mg of benzotriazol-1-yl-oxytris(dimethylamino)-phosphonium hexafluorophosphate and 14 µl of morpholine were added in succession at room temperature and the mixture was subsequently stirred at room temperature for 16 hours. The mixture was partitioned between-ethyl acetate and water, the organic phase was dried over sodium sulphate, concentrated on a rotary evaporator and the residue was chromatographed over silica gel with $CH_2Cl_2$/MeOH (30/1) as the eluent. There was thus obtained N-[3-(2-hydroxy-ethoxy)-2-(2-methoxy-phenoxy)-5-(morpholine-4-carbonyl)-phenyl]-4-methyl-benzenesulphonamide (71 mg) as a white foam.

EXAMPLE 64

A solution of 57 mg of methyl 3-(2-hydroxy-ethoxy)-4-(2-methoxy-phenoxy)-5-(toluene-4-sulphonylamino)-benzoate, 51 mg of 2-pyridylcarboxylic acid azide and 5 mg of p-dimethylaminopyridine in toluene (5 ml) was heated at 110° C. (bath temperature) for 1 hour. The residue was partitioned between ethyl acetate and 1N HCl solution, the aqueous phase was extracted several times with methylene chloride and the organic phase was dried over magnesium sulphate. The solvent was finally removed on a rotary evaporator and the crude product was chromatographed over silica gel with $CH_2Cl_2$/ethyl acetate (12/1) as the eluent. There was thus obtained methyl 4-(2-methoxy-phenoxy)-3-[2-(pyridin-2-ylcarbamoyloxy)-ethoxy]-5-(toluene-4-sulphonylamino)-benzoate as a white solid.

EXAMPLE 65

In analogy to Example 64, from N-[3-(2-hydroxy-ethoxy)-2-(2-methoxy-phenoxy)-5-(morpholine-4-carbonyl)-phenyl]-4-methyl-benzenesulphonamide and 2-pyridylcarboxylic acid azide there was obtained pyridin-2-yl-carbamic acid 2-[2-(2-methoxy-phenoxy)-5-(morpholine-4-carbonyl)-3-(toluene-4-sulphonylamino)-phenoxy]-ethyl ester.

EXAMPLE 66 a) 1.13 g of methyl 3-amino-4-(2-chloro-5-methoxy-phenoxy)-5-[2-(tetrahydro-pyran-2-yloxy)-ethoxy]-benzoate were dissolved in a mixture of toluene/pyridine (20 ml/30 ml) treated dropwise while cooling with ice with a solution of 1.05 g of 4-tert.butyl-benzenesulphonyl chloride in toluene (30 ml) and subsequently stirred at RT for 24 hours. The reaction mixture was poured on to ice/3M HCl, the product was extracted with ethyl acetate and the organic phase was dried over magnesium sulphate. After removing the solvent there was obtained methyl 3-(4-tert-butyl-benzenesulphonylamino)-4-(2-chloro-5-methoxy-phenoxy)-5-[2-(tetrahydro-pyran-2-yloxy)-ethoxy]-benzoate as a yellow solid.

b) A solution of 1.62 g of methyl 3-(4-tert-butyl-benzenesulphonylamino)-4-(2-chloro-5-methoxy-phenoxy)-5-[2-(tetrahydro-pyran-2-yloxy)-ethoxy]-benzoate in methanol (30 ml) was treated at room temperature with 3.5 ml of 5.5M aqueous HCl and the solution was subsequently stirred at RT for a further 3.5 hours. The solvent was removed on a rotary evaporator and the residue was taken up in ethyl acetate and washed with 2N potassium hydrogen carbonate solution. The organic phase was dried over magnesium sulphate, the solvent was removed on a rotary evaporator and the crude product was chromatographed over silica gel with $CH_2Cl_2$/ethyl acetate (9/1) as the eluent. There was thus obtained methyl 3-(4-tert-butylbenzene-sulphonylamino)-4-(2-chloro-5-methoxy-phenoxy)-5-(2-hydroxy-ethoxy)-benzoate.
Preparation of the Starting Material:

c) 3.59 9 of methyl 4-chloro-3-nitro-5-[2-(tetrahydro-pyran-2-yloxy)-ethoxy]-benzoate were dissolved in acetone (200 ml), treated at RT with 4.14 g of potassium carbonate, 1.9 g of 2-chloro-5-methoxy-phenol and the mixture was subsequently heated at reflux for 20 hours. The mixture was poured on to ice-water and extracted with ethyl acetate. The organic phase was washed 3 times with 5% sodium hydroxide solution and then with water, dried over sodium sulphate and finally concentrated on a rotary evaporator. The crude product (5.5 g) was flash chromatographed on silica gel with hexane/ether (1/1) as the eluent. There was thus obtained methyl 4-(2-chloro-5-methoxy-phenoxy)-3-nitro-5-[2-(tetrahydro-pyran-2-yloxy)-ethoxy]-benzoate (3.5 g) as a pale yellow powder.

d) 3.5 g of methyl 4-(2-chloro-5-methoxy-phenoxy)-3-nitro-5-[2-(tetrahydro-pyran-2-yloxy)-ethoxy]-benzoate were dissolved in methanol (150 ml), treated with 0.5 g of Ra-Ni catalyst and hydrogenated at room temperature for 1.5 hours. The catalyst was filtered off and the solution was concentrated on a rotary evaporator There was thus obtained methyl 3-amino-4-(2-chloro-5-methoxy-phenoxy)-5-[2-(tetrahydro-pyran-2-yloxy)-ethoxy]-benzoate.

Pale yellow solid.

EXAMPLE 67

1.13 g of methyl 3-(4-tert-butylbenzenesulphonylamino)-4-(2-chloro-5-methoxy-phenoxy)-5-(2-hydroxy-ethoxy)-benzoate were dissolved in methanol (30 ml), treated with 6 ml of 1M NaOH solution and subsequently heated at reflux for 6 hours. The mixture was poured on to ice-water, acidified with dilute HCl solution (pH 1) and the product was extracted with ethyl acetate. The organic phase was dried over sodium sulphate, concentrated and the solid obtained was dried in a high vacuum. There was thus obtained 3-(4-tert-butyl-benzenesulphonylamino)-4-(2-chloro-5-methoxy-phenoxy)-5-(2-hydroxy-ethoxy)-benzoic acid as a white, crystalline solid.

EXAMPLE 68

55 mg of of 3-(4-tert-butyl-benzenesulphonylamino)-4-(2-chloro-5-methoxy-phenoxy)-5-(2-hydroxy-ethoxy)-benzoic acid were dissolved in acetonitrile (5 ml), 19 µl of n-ethyldiisopropylamine, 49 mg of benzotriazol-1-yl-oxytris (dimethylamino)-phosphonium hexafluorophosphate and, 10 µl of morpholine were added in succession at RT and the mixture was subsequently stirred at RT for 2 hours. The mixture was partitioned between ethyl acetate and water, the organic phase was dried over sodium sulphate, concentrated on a rotary evaporator and the residue was chromatographed over silica gel with $CH_2Cl_2$/MeOH (20/1) as the eluent. There was thus obtained 4-tert-butyl-N-[2-(2-chloro-5-methoxy-phenoxy)-3-(2-hydroxy-ethoxy)-5-(morpholine-4-carbonyl)-phenyl]-benzenesulphonamide (63 mg) as a white foam.

EXAMPLE 69

In analogy to Example 68, from 3-(4-tert-butylbenzene-sulphonylamino)-4-(2-chloro-5-methoxy-phenoxy)-5-(2-hydroxy-ethoxy)-benzoic acid and aniline there was obtained 3-(4-tert-butyl-benzenesulphonylamino)-4-(2-chloro-5-methoxy-phenoxy)-5-(2-hydroxy-ethoxy)-N-phenyl-benzamide.

EXAMPLE 70

A solution of 28 mg of methyl 3-(4-tert-butyl-benzenesulphonylamino)-4-(2-chloro-5-methoxy-phenoxy)-5-(2-hydroxy-ethoxy)-benzoate, 22 mg of 2-pyridylcarboxylic acid azide and 2 mg of p-dimethylaminopyridine in toluene (5 ml) was heated at 110° C. (bath temperature) for 1.5 hours. The residue was partitioned between ethyl acetate and 1N HCl solution, the aqueous phase was extracted several times with methylene chloride and the organic phase was dried over magensium sulphate. The solvent was finally removed on a rotary evaporator and the crude product was chromatographed over silica gel with $CH_2Cl_2$/ethyl acetate (10/1) as the eluent. There was thus obtained methyl 3-(4-tert-butyl-benzenesulphonylamino)-4-( 2-chloro-5-methoxy-phenoxy)-5-[2-(pyridin-2-ylcarbamoyloxy)-ethoxy]-benzoate as a white solid.

EXAMPLE 71

In analogy to Example 70, from 4-tert-butyl-N-[2-(2-chloro-5-methoxy-phenoxy)-3-(2-hydroxy-ethoxy)-5-

(morpholine-4-carbonyl)-phenyl]-benzenesulphonamide and 2-pyridylcarboxylic acid azide there was obtained pyridin-2-yl-carbamic acid 2-[3-(4-tert-butyl-benzenesulphonylamino)-2-(2-chloro-5-methoxy-phenoxy)-5-(morpholine-4-carbonyl)-phenoxy]-ethyl ester.

EXAMPLE 72 a) 1.12 g of methyl 3-amino-4-(2-chloro-5-methoxy-phenoxy)-5-[2-(tetrahydro-pyran-2-yloxy)-ethoxy]-benzoate were dissolved in a mixture of toluene/pyridine (20 ml/30 ml) treated dropwise while cooling with ice with a solution of 1.05 g of 5-isopropylpyridine-2-sulphonyl chloride in toluene (30 ml) and subsequently stirred at room temperature for 24 hours. The reaction mixture was poured on to ice/3M HCl, the product was extracted with ethyl acetate and the organic phase was washed with water and dried over magnesium sulphate. After removing the solvent there was obtained the desired methyl 4-(2-chloro-5-methoxy-phenoxy)-3-(5-isopropyl-pyridine-2-sulphonylamino)-5-[2-(tetrahydro-pyran-2-yloxy)-ethoxy]-benzoate as a yellow solid.

b) A solution of 2.0 g of methyl 4-(2-chloro-5-methoxy-phenoxy)-3-(5-isopropyl-pyridin-2-sulphonylamino)-5-[2-(tetrahydro-pyran-2-yloxy)-ethoxy]-benzoate in methanol (10 ml) was treated at RT with 5 ml of 5.5M aqueous HCl and the solution was subsequently stirred at RT for a further 1 hour. The solvent was removed on a rotary evaporator and the residue was taken up in ethyl acetate and washed with 2N potassium hydrogen carbonate solution. The organic phase was dried over magnesium sulphate, the solvent was removed on a rotary evaporator and the crude product was chromatographed over silica gel with $CH_2Cl_2$/ethyl acetate (10/1) as the eluent. There was thus obtained methyl 4-(2-chloro-5-methoxy-phenoxy)-3-(2-hydroxy-ethoxy)-5-(5-isopropyl-pyridine-2-sulphonylamino)-benzoate.

EXAMPLE 73

0.905 g of 4-(2-chloro-5-methoxy-phenoxy)-3-(2-hydroxy-ethoxy)-5-(5-isopropyl-pyridine-2-sulphonylamino)-benzoate was dissolved in methanol (10 ml), treated with 6.57 ml of 1M NaOH solution and subsequently heated at reflux for 1 hour. The mixture was poured on to ice-water, acidified with dilute HCl solution (pH 1) and the product was extracted with ethyl acetate. The organic phase was washed once with water, dried over sodium sulphate and concentrated The solid obtained was dried in a high vacuum. There was thus obtained 4-(2-chloro-5-methoxy-phenoxy)-3-(2-hydroxy-ethoxy)-5-(5-isopropyl-pyridine-2-sulphonylamino)-benzoic acid as a white, crystalline solid, 1.05 g.

EXAMPLE 74

54 mg of 4-(2-chloro-5-methoxy-phenoxy)-3-(2-hydroxy-ethoxy)-5-(5-isopropyl-pyridine-2-sulphonylamino)-benzoic acid were dissolved in acetonitrile (5 ml), 19 µl of n-ethyldiisopropylamine, 49 mg of benzotriazol-1-yl-oxytris(dimethylamino)-phosphonium hexafluorophosphate and 10 µl of morpholine were added in succession at RT and the mixture was subsequently stirred at RT for 2 hours. The mixture was partitioned between ethyl acetate and water, the organic phase was dried over sodium sulphate, concentrated on a rotary evaporator and the residue was chromatographed over silica gel with $CH_2Cl_2$/MeOH (25/1) as the eluent. There was thus obtained 5-isopropyl-pyridine-2-sulphonic acid [2-(2-chloro-5-methoxy-phenoxy)-3-(2-hydroxy-ethoxy)-5-(morpholine-4-carbonyl)-phenyl]-amide (60 mg) as a white foam.

EXAMPLE 75

A solution of 55 mg of methyl 4-(2-chloro-5-methoxy-phenoxy)-3-(2-hydroxy-ethoxy)-5-(5-isopropyl-pyridine-2-sulphonylamino)-benzoate, 44 mg of 2-pyridylcarboxylic acid azide and 4 mg of p-dimethylaminopyridine in toluene (5 ml) was heated at 110 C (bath temperature) for 1 hour. The residue was partitioned between ethyl acetate and 1N HCl solution, the aqueous phase was extracted several times with ethyl acetate and the organic phase was dried over magnesium sulphate. The solvent was finally removed on a rotary evaporator and the crude product was chromatographed over silica gel with $CH_2Cl_2$/ethyl acetate (10/1) as the eluent. There was thus obtained methyl 4-(2-chloro-5-methoxy-phenoxy)-3-(5-isopropyl-pyridine-2-sulphonylamino)-5-[2-(pyridin-2-ylcarbamoyloxy)-ethoxy]-benzoate as a white solid.

EXAMPLE 76

In analogy to Example 75, from 5-isopropyl-pyridine-2-sulphonic acid [2-(2-chloro-5-methoxy-phenoxy)-3-(2-hydroxy-ethoxy)-5-(morpholine-4-carbonyl)-phenyl]-amide and 2-pyridylcarboxylic acid azide there was obtained pyridin-2-yl-carbamic acid 2-[2-(2-chloro-5-methoxy-phenoxy)-3-(5-isopropyl-pyridine-2-sulphonylamino)-5-(morpholine-4-carbonyl)-phenoxy]-ethyl ester.

EXAMPLE 77 a) 135 mg of methyl 3-amino-4-(2-chloro-5-methoxy-phenoxy)-5-[2-(tetrahydro-pyran-2-yloxy)-ethoxy]-benzoate were dissolved in pyridine (3 ml), treated while cooling with ice with a solution of 111 mg of 4-methoxy-benzenesulphonyl chloride in toluene (1 ml) and subsequently stirred at RT for 20 hours. The reaction mixture was poured on to ice/3M HCl, the product was extracted with ethyl acetate and the organic phase was washed with water and dried over magnesium sulphate. After removing the solvent there was obtained methyl 4-(2-chloro-5-methoxy-phenoxy)-3-(4-methoxy-benzenesulphonylamino)-5-[2-(tetrahydro-pyran-2-yloxy)-ethoxy]-benzoate as a foam.

b) A solution of 88 mg of 4-(2-chloro-5-methoxy-phenoxy)-3-(4-methoxy-benzenesulphonylamino)-5-[2-(tetrahydro-pyran-2-yloxy)-ethoxy]-benzoate in methanol (5 ml) was treated at RT with 1 ml of 5.5M aqueous HCl and the solution was subsequently stirred at RT for a further 1.5 hours. The solvent was removed on a rotary evaporator and the residue was taken up in ethyl acetate and washed with 2N potassium hydrogen carbonate solution. The organic phase was dried over magnesium sulphate, the solvent was removed on a rotary evaporator and the crude product was chromatographed over silica gel with $CH_2Cl_2$/ethyl acetate (10/1) as the eluent. There was thus obtained methyl 4-(2-chloro-5-methoxy-phenoxy)-3-(2-hydroxy-ethoxy)-5-(4-methoxy-benzenesulphonylamino)-benzoate.

EXAMPLE 78

Analogously to Example 73, by basic saponification of methyl 4-(2-chloro-5-methoxy-phenoxy)-3-(2-hydroxy-ethoxy)-5-(4-methoxybenzenesulphonylamino)-benzoate with 1M NaOH there was obtained 4-(2-chloro-5-methoxy-phenoxy)-3-(2-hydroxy-ethoxy)-5-(4-methoxy-benzenesulphonylamino)-benzoic acid.

EXAMPLE 79

Analogously to Example 74, by condensing 4-(2-chloro-5-methoxy-phenoxy)-3-(2-hydroxy-ethoxy)-5-(4-methoxybenzenesulphonylamino)-benzoic acid with aniline there was obtained 4-(2-chloro-5-methoxy-phenoxy)-3-(2-hydroxy-ethoxy)-5-(4-methoxy-benzenesulphonylamino)-N-phenyl-benzamide.

EXAMPLE 80

Analogously to Example 77, by condensing methyl 3-amino-4-(2-chloro-5-methoxy-phenoxy)-5-[2-(tetrahydro-pyran-2-yloxy)-ethoxy]-benzoate with benzo[1,3]dioxol-5-sulphonyl chloride there was obtained methyl 3-(benzo[1,3]dioxol-5-sulphonyl-amino)-4-(2-chloro-5-methoxy-phenoxy)-5-[2-(tetrahydro-pyran-2-yloxy)-ethoxy]-benzoate und therefrom by treatment with 5.5M HCl there was obtained methyl 3-(benzo[1,3]dioxol-5-sulphonylamino)-4-(2-chloro-5-methoxy-phenoxy)-5-(2-hydroxy-ethoxy)-benzoate.

EXAMPLE 81

Analogously to Example 73, by basic saponification of methyl 3-(benzo-[1,3]dioxol-5-sulphonylamino)-4-(2-chloro-5-methoxy-phenoxy)-5-(2-hydroxy-ethoxy)-benzoate with 1M NaOH there was obtained 3-(benzo[1,3]dioxol-5-sulphonylamino)-4-(2-chloro-5-methoxy-phenoxy)-5-(2-hydroxy-ethoxy)-benzoic acid.

EXAMPLE 82

Analogously to Example 74, by condensing 3-(benzo[1,3]-dioxol-5-sulphonylamino)-4-(2-chloro-5-methoxy-phenoxy)-5-(2-hydroxy-ethoxy)-benzoic acid with aniline there was obtained 3-(benzo[1,3]dioxol-5-sulphonylamino)-4-(2-chloro-5-methoxy-phenoxy)-5-(2-hydroxy-ethoxy)-N-phenyl-benzamide.

EXAMPLE 83

Analogously to Example 77, by condensing methyl 3-amino-4-(2-chloro-5-methoxy-phenoxy)-5-[2-(tetrahydro-pyran-2-yloxy)-ethoxy]-benzoate with 4-(trifluoromethyl)-benzenesulphonyl chloride there was obtained methyl 4-(2-chloro-5-methoxy-phenoxy)-3-[2-(tetrahydro-pyran-2-yloxy)-ethoxy]-5-(4-trifluoromethyl-benzenesulphonylamino)-benzoate and therefrom by treatment with 5.5M HCl there was obtained methyl 4-(2-chloro-5-methoxy-phenoxy)-3-(2-hydroxy-ethoxy)-5-(4-trifluoromethyl-benzenesulphonylamino)-benzoate.

EXAMPLE 84

Analogously to Example 73, by basic saponification of methyl 4-(2-chloro-5-methoxy-phenoxy)-3-(2-hydroxy-ethoxy)-5-(4-trifluoromethyl-benzenesulphonylamino)-benzoate with 1M NaOH there was obtained the desired 4-(2-chloro-5-methoxy-phenoxy)-3-(2-hydroxy-ethoxy)-5-(4-trifluoromethyl-benzenesulphonylamino)-benzoic acid.

EXAMPLE 85

Analogously to Example 74, by condensing 4-(2-chloro-5-methoxy-phenoxy)-3-(2-hydroxy-ethoxy)-5-(4-trifluoromethyl-benzenesulphonylamino)-benzoic acid with aniline there was obtained 4-(2-chloro-5-methoxy-phenoxy)-3-(2-hydroxy-ethoxy)-N-phenyl-5-(4-trifluoromethyl-benzenesulphonylamino)-benzamide.

EXAMPLE 86 a) 0.35 9 of methyl 3-amino-4-(3-methoxy-phenoxy)-5-[2-(tetrahydro-pyran-2-yloxy)-ethoxy]-benzoate was dissolved in pyridine (10 ml), treated dropwise while cooling with ice with a solution of 0.312 g of 4-tert.butyl-benzenesulphonyl chloride in toluene (3 ml) and subsequently stirred at RT for 24 hours. The reaction mixture was poured on to ice/3M HCl, the product was extracted with ethyl acetate, the organic phase was washed with 2M $KHCO_3$ solution and dried over magnesium sulphate. After removing the solvent there was obtained the desired methyl 3-(4-tert-butyl-benzenesulphonylamino)-4-(3-methoxy-phenoxy)-5-[2-(tetrahydro-pyran-2-yloxy)-ethoxy]-benzoate as a solid.

b) A solution of 0.566 g of methyl 3-(4-tert-butyl-benzenesulphonylamino)-4-(3-methoxy-phenoxy)-5-[2-(tetrahydro-pyran-2-yloxy)-ethoxy]-benzoate in methanol (7 ml) was treated at RT with 5 ml of 5.5M aqueous HCl and the solution was subsequently stirred at RT for a further 1 hour. The solvent was removed on a rotary evaporator and the residue was taken up in ethyl acetate and washed with 2N potassium hydrogen carbonate solution. The organic phase was dried over magnesium sulphate, the solvent was removed on a rotary evaporator and the crude product was chromatographed over silica gel with $CH_2Cl_2$/acetone (50/1) as the eluent. There was thus obtained 0.113 g of methyl 3-(4-tert-butyl-benzenesulphonylamino)-5-(2-hydroxy-ethoxy)-4-(3-methoxy-phenoxy)-benzoate.

Preparation of the Starting Material:

c) 3.57 g of methyl 4-chloro-3-nitro-5-[2-(tetrahydro-pyran-2-yloxy)-ethoxy]-benzoate were dissolved in acetone (100 ml), treated at RT with 4.15 g of potassium carbonate, 2.82 ml of 3-methoxy-phenol and the mixture was subsequently heated at reflux for 20 hours. The mixture was poured on to ice-water and extracted with ethyl acetate. The organic phase was washed 3 times with 5% sodium hydroxide solution then with water, dried over sodium sulphate and finally concentrated on a rotary evaporator. The crude product (5.5 g) was flash chromatographed on silica gel with hexane/ether (1/1) as the eluent. There was thus obtained methyl 3-nitro-4-(3-methoxy-phenoxy)-5-[2-(tetrahydro-pyran-2-yloxy)-ethoxy]-benzoate as a pale yellow powder.

d) 3.5 g of methyl 3-nitro-4-(3-methoxy-phenoxy)-5-[2-(tetrahydro-pyran-2-yloxy)-ethoxy]-benzoate were dissolved in methanol (100 ml), treated with 0.5 g of Ra-Ni catalyst and hydrogenated at room temperature for 1 hour. The catalyst was filtered off and the solution was concentrated on a rotary evaporator. There was thus obtained the desired methyl 3-amino-4-(3-methoxy-phenoxy)-5-[2-(tetrahydro-pyran-2-yloxy)-ethoxy]-benzoate as a pale yellow solid.

EXAMPLE 87

Analogously to Example 73, by basic saponification of methyl 3-(4-tert-butyl-benzenesulphonylamino)-5-(2-hydroxy-ethoxy)-4-(3-methoxy-phenoxy)-benzoate with 1M NaOH there was obtained 3-(4-tert-butyl-benzenesulphonylamino)-5-(2-hydroxy-ethoxy)-4-(3-methoxy-phenoxy)-benzoic acid.

EXAMPLE 88

Analogously to Example 74, by condensing 3-(4-tert-butyl-benzenesulphonylamino)-5-(2-hydroxy-ethoxy)-4-(3-methoxy-phenoxy)-benzoic acid with morpholine there was obtained 4-tert-butyl-N-[3-(2-hydroxy-ethoxy)-2-(3-methoxy-phenoxy)-5-(morpholine-4-carbonyl)-phenyl]-benzenesulphonamide.

EXAMPLE 89

Analogously to Example 74, by condensing 3-(4-tert-butyl-benzenesulphonylamino)-5-(2-hydroxy-ethoxy)-4-(3- methoxy-phenoxy)-benzoic acid with aniline there was obtained 3-(4-tert-butylbenzenesulphonylamino)-5-(2-hydroxy-ethoxy)-4-(3-methoxy-phenoxy)-N-phenyl-benzamide.

EXAMPLE 90

Analogously to Example 74, by condensing 3-(4-tert-butyl-benzenesulphonylamino)-5-(2-hydroxy-ethoxy)-4-(3-methoxy-phenoxy)-benzoic acid with 2-aminobiphenyl there was obtained N-biphenyl-2-yl-3-(4-tert-butyl-benzenesulphonylamino)-5-(2-hydroxy-ethoxy)-4-(3-methoxy-phenoxy)-benzamide.

EXAMPLE 91

Analogously to Example 74, by condensing 3-(4-tert-butyl-benzenesulphonylamino)-5-(2-hydroxy-ethoxy)-4-(3-methoxy-phenoxy)-benzoic acid with anisidine there was obtained 3-(4-tert-butyl-benzenesulphonylamino)-5-(2-hydroxy-ethoxy)-4-(3-methoxy-phenoxy)-N-(3-methoxy-phenyl)-benzamide.

EXAMPLE 92

Analogously to Example 74, by condensing 3-(4-tert-butyl-benzenesulphonylamino)-5-(2-hydroxy-ethoxy)-4-(3-methoxy-phenoxy)-benzoic acid with L-leucine methyl ester there was obtained methyl 2-[3-(4-tert-butyl-benzenesulphonylamino)-5-(2-hydroxy-ethoxy)-4-(3-methoxy-phenoxy)-benzoylamino]-4-methyl-pentanoate.

EXAMPLE 93

Analogously to Example 74, by condensing 3-(4-tert-butyl-benzenesulphonylamino)-5-(2-hydroxy-ethoxy)-4-(3-methoxy-phenoxy)-benzoic acid with 3,4-methylenedioxyaniline there was obtained N-benzo-[1,3]dioxol-5-yl-3-(4-tert-butylbenzenesulphonylamino)-5-(2-hydroxy-ethoxy)-4-(3-methoxy-phenoxy)-benzamide.

EXAMPLE 94

37.5 mg of methyl 2-[3-(4-tert-butyl-benzenesulphonylamino)-5-(2-hydroxy-ethoxy)-4-(3-methoxy-phenoxy)-benzoylamino]-4-methyl-pentanoate were dissolved in methanol (5 ml), treated at room temperature with 0.23 ml of 1M NaOH solution and stirred at room temperature for one hour and at 60° C. for 3.5 hours. The solution was poured on to ice/water, adjusted to pH 1 with dilute HCl solution and the product was extracted with ethyl acetate. The organic phase was dried over magnesium sulphate, the solvent was removed on a rotary evaporator and the residue was dried in a high vacuum. There was thus obtained 2-[3-(4-tert-butyl-benzenesulphonylamino)-5-(2-hydroxy-ethoxy)-4-(3-methoxy-phenoxy)-benzoylamino]-4-methyl-pentanoic acid as a white solid.

EXAMPLE 95

In analogy to Example 75, from methyl 3-(4-tert-butyl-benzenesulphonylamino)-5-(2-hydroxy-ethoxy)-4-(3-methoxy-phenoxy)-benzoate and 2-pyridylcarboxylic acid azide there was obtained methyl 3-(4-tert-butyl-benzenesulphonylamino)-4-(3-methoxy-phenoxy)-5-[2-(pyridin-2-ylcarbamoyloxy)-ethoxy]-benzoate.

EXAMPLE 96

In analogy to Example 75, from 4-tert-butyl-N-[3-(2-hydroxy-ethoxy)-2-(3-methoxy-phenoxy)-5-(morpholine-4-carbonyl)-phenyl]-benzenesulphonamide and 2-pyridylcarboxylic acid azide there was obtained pyridin-2-yl-carbamic acid 2-[3-(4-tert-butyl-benzenesulphonylamino)-2-(3-methoxy-phenoxy)-5-(morpholine-4-carbonyl)-phenoxy]-ethyl ester.

EXAMPLE 97

In analogy to Example 75, from 3-(4-tert-butyl-benzenesulphonylamino)-5-(2-hydroxy-ethoxy)-4-(3-methoxy-phenoxy)-N-(3-methoxy-phenyl)-benzamide and 2-pyridylcarboxylic acid azide there was obtained pyridin-2-yl-carbamic acid 2-[3-(4-tert-butyl-benzenesulphonylamino)-2-(3-methoxy-phenoxy)-5-(3-methoxy-phenylcarbamoyl)-phenoxy]-ethyl ester.

EXAMPLE 98

In analogy to Example 75, from 3-(4-tert-butyl-benzenesulphonylamino)-5-(2-hydroxy-ethoxy)-4-(3-methoxy-phenoxy)-N-phenyl-benzamide and 2-pyridylcarboxylic acid azide there was obtained the desired pyridin-2-yl-carbamic acid 2-[3-(4-tert-butyl-benzenesulphonylamino)-2-(3-methoxy-phenoxy)-5-phenyl-carbamoyl-phenoxy]-ethyl ester.

MS: 711.3 (M+H).

EXAMPLE 99

Analogously to Example 86, by condensing methyl 3-amino-4-(3-methoxy-phenoxy)-5-[2-(tetrahydro-pyran-2-yloxy)-ethoxy]-benzoate with 4-methoxybenzenesulphonyl chloride there was obtained methyl 3-(4-methoxy-benzenesulphonyl-amino)-4-(3-methoxy-phenoxy)-5-[2-(tetrahydro-pyran-2-yloxy)-ethoxy]-benzoate and therefrom by treatment with 5.5M HCl there was obtained methyl 3-(2-hydroxy-ethoxy)-5-(4-methoxy-benzenesulphonylamino)-4-(3-methoxy-phenoxy)-benzoate.

EXAMPLE 100

Analogously to Example 73, by basic saponification of methyl 3-(2-hydroxy-ethoxy)-5-(4-methoxy-benzenesulphonylamino)-4-(3-methoxy-phenoxy)-benzoate with 1M NaOH there was obtained 3-(2-hydroxy-ethoxy)-5-(4-methoxy-benzenesulphonylamino)-4-(3-methoxy-phenoxy)-benzoic acid.

EXAMPLE 101

Analogously to Example 74, condensing 3-(2-hydroxy-ethoxy)-5-(4-methoxy-benzenesulphonylamino)-4-(3-methoxy-phenoxy)-benzoic acid with aniline there was obtained 3-(2-hydroxy-ethoxy)-5-(4-methoxy-benzenesulphonylamino)-4-(3-methoxy-phenoxy)-N-phenyl-benzamide.

EXAMPLE 102

In analogy to Example 75, from 3-(2-hydroxy-ethoxy)-5-(4-methoxy-benzenesulphonylamino)-4-(3-methoxy-phenoxy)-N-phenyl-benzamide and 2-pyridylcarboxylic acid azide there was obtained pyridin-2-yl-carbamic acid 2-[3-(4-methoxy-benzenesulphonylamino)-2-(3-methoxy-phenoxy)-5-phenylcarbamoyl-phenoxy]-ethyl ester.

EXAMPLE 103

Analogously to Example 86, by condensing methyl 3-amino-4-(3-methoxy-phenoxy)-5-[2-(tetrahydro-pyran-2- yloxy)-ethoxy]-benzoate with 4-methylsulphanylbenzenesulphonyl chloride there was obtained methyl 4-(3-methoxy-phenoxy)-3-(4-methylsulphanyl-benzenesulphonylamino)-5-[2-(tetrahydro-pyran-2-yloxy)-ethoxy]-benzoate and therefrom by treatment with 5.5M HCl there was obtained methyl 3-(2-hydroxy-ethoxy)-4-(3-methoxy-phenoxy)-5-(4-methylsulphanyl-benzenesulphonylamino)-benzoate.

EXAMPLE 104

Analogously to Example 73, by basic saponification of methyl 3-(2-hydroxy-ethoxy)-4-(3-methoxy-phenoxy)-5-(4-methylsulphanyl-benzene-sulphonylamino)-benzoate with 1M NaOH there was obtained 3-(2-hydroxy-ethoxy)-4-(3-methoxy-phenoxy)-5-(4-methylsulphanyl-benzenesulphonylamino)-benzoic acid.

EXAMPLE 105

Analogously to Example 74, by condensing 3-(2-hydroxy-ethoxy)-4-(3-methoxy-phenoxy)-5-(4-methylsulphanyl-benzene-sulphonyl-amino)-benzoic acid with aniline there was obtained 3-(2-hydroxy-ethoxy)-4-(3-methoxy-phenoxy)-5-(4-methyl-sulphanyl-benzenesulphonyl-amino)-N-phenyl-benzamide.

EXAMPLE 106

By hydrogenating benzyl {3-(4-tert-butyl-benzenesulphonylamino)-4-(2-methoxy-phenoxy)-5-[2-(pyridin-2-ylcarbamoyloxy)-ethoxy]-benzoylamino}-acetate, described in Example 18, in methanol over palladium/charcoal at RT and under normal pressure there was obtained {3-(4-tert-butyl-benzenesulphonylamino)-4-(2-methoxy-phenoxy)-5-[2-(pyridin-2-ylcarbamoyloxy)-ethoxy]-benzoylamino}-acetic acid.

EXAMPLE 107

A mixture of 290 mg of p-tert-butyl-N-[2-(2-hydroxy)-3-(o-methoxyphenoxy)-6-methyl-4-pyridyl]benzenesulphonamide, 341 mg of iodoethanol, 362 mg of silver carbonate and 25 ml of toluene was heated to 1000 under reflux for 5 hrs., with a further 150 mg of iodoethanol being added thereto after 4 hrs. The reaction mixture was filtered and the filtrate was evaporated in a vacuum. The residue was chromatographed on 30 g of silica gel. With $CH_2Cl_2$+1% methanol there could be isolated 110 mg of pure amorphous p-tert-butyl-N-[2-(2-hydroxyethoxy)-3-(o-methoxyphenoxy)-6-methyl-4-pyridyl-]benzenesulphonamide.

Mass spectrum: $M^t/e$=486. IR spectrum: bands at 3211, 2963, 1600, 1498, 1339, 1252, 839, 751 $cm^{-1}$.

The starting material was prepared as follows:

3-aminocrotononitrile was converted with ethylmagnesium bromide and subsequently with o-methoxyphenoxy-acetyl chloride into 3-(o-methoxyphenoxyacetyl-amino)-crotononitrile, which was cyclized with $NaNH_2$ in dioxan at 100° C. into 2-hydroxy-3-(O-methoxyphenoxy)-4-amino-6-methyl-pyridine. Reaction with 4-tert-butylbenzenesulphonyl chloride in pyridine at 1 O0° C. gave 2-(p-tert-butylphenylsulphonyloxy)-3-(o-methoxyphenoxy)-4-(p-tert-butylphenyl-sulphonamide-6-methyl-pyridine. Treatment with sodium hydroxide in ethanol led to p-tert-butyl-N-[2-(2-hydroxy)-3-(o-methoxyphenoxy)-6-methyl-4-pyridyl]benzenesulphonamide, amorphous, MS spectrum: $M^t/e$=442; NMR spectrum: 1.29(S)(9H,—$C(CH_3)_3$); 2.21(5,6-methyl); 4.01(s, $OCH_3$).

EXAMPLE 108

In analogy to Example 107, from 270 mg of p-tert butyl-N-[2-(2-hydroxy)-3-(3-methoxyphenoxy)-6-methyl-4-pyridyl]benzenesulphonamide there were obtained 122 mg of pure p-tert-butyl-N-[2-(2-hydroxyethoxy)-3-(3-methoxy-phenoxy)-6-methyl-4-pyridyl] benzenesulphonamide of m.p. 138–139° C. (acetone/hexane).

IR spectrum: bands at 3259, 2963, 1601, 1490, 1340, 1177, 836, 571 $cm^{-1}$.

The starting material was prepared analogously to Example 107 using M-methoxyphenoxy-acetyl chloride.

MS spectrum: $M^t/e$=442; NMR spectrum: 1.32(5,9H,—$C(CH_3)_3$); 2.09(s, 3H, 6-methyl); 3.75 (s, 3H, $OCH_3$).

EXAMPLE 109

In analogy to Example 107, from 200 mg of p-tert-butyl-N-[2-(2-hydroxyl]benzenesulphonamide there were obtained 163 mg of pure 4-tert-butyl-N-[2-(2-hydroxyethoxy)-3-(2-methoxyphenoxy)-6-phenyl-pyrid-4-yl]-benzenesulphonamide.

IR spectrum: bands at 2964, 1597, 1339, 1168, 1100, 750 $cm^{-1}$.

The starting material was prepared analogously to Example 107 using 3-amino-3-phenyl-acrylonitrile and o-methoxyphenoxy-acetyl chloride.

M spectrum: $m^t/e$=308; IR spectrum: bands at 3442, 1617, 1499, 1251, 1217, 771 $cm^{-1}$.

EXAMPLE 110

In analogy to Example 107, from 500 mg of N-[2-(2-hydroxy)-3-(2-methoxyphenoxy)-6-methylpyridin-4-yl]-5-isopropyl-pyridine-2-sulphonamide there were obtained 194 mg of pure, amorphous N-[2-(2-hydroxyethoxy)-3-(2-methoxyphenoxy)-6-methyl-pyridin-4-yl]-5-isopropyl-pyridine-2-sulphonamide.

IR spectrum: bands at 3201, 2930, 1601, 1498, 1253, 1180, 847, 750 $cm^{-1}$.

The starting material was prepared analogously to Example 1 using 5-isopropyl-pyridyl-2-sulphonyl chloride.

MS spectrum: $M^t/e$=429.

EXAMPLE 111

A mixture of 93 mg of N-[2-(2-hydroxyethoxy)-3-(2-methoxyphenoxy)-6-methyl-pyridin-4-yl]-5-isopropyl-pyridine-2-sulphonamide, 43 mg of pyridine-2-carboxylic acid azide, 10 ml of toluene and 10 mg of 4-dimethylamino-pyridine was heated to reflux for 90 minutes. The reaction mixture was evaporated in vac., dissolved in methylene chloride, washed with water, dried with magnesium sulphate and evaporated. The residue was chromatographed on 20 g of silica gel with methylene chloride. There could be isolated 96 mg of pure, amorphous pyridin-2-yl-carbamic acid 2-[4-(5-isopropyl-pyridine-2-sulphonylamino)-3-(2-methoxy-phenoxy)-6-methyl-pyridin-2-yloxy]ethyl.

MS spectrum: $M^t/e$=594; IR spectrum: bands at 2963, 1734, 1596, 1438, 1181, 847 $cm^{-1}$.

EXAMPLE 112

Analogously to Example 111, from 40 mg of 4-tert-butyl-N-[2-(2-hydroxyethoxy)-3-(2-methoxyphenoxy)-6-phenyl-pyrid-4-yl]-benezensulphonamide there were obtained 33 mg of pure, amorphous pyridin-2-yl-carbamic acid 2[4(4- tert-butyl-benzenesulphonamino)-3-(2-methoxyphenoxy)-6-phenyl-pyridin-2-yloxy]-ethyl ester.

MS spectrum: M$^{t/}$e=668; IR spectrum: bands at 2964, 1735,1596,1439, 1169, 777 cm$^{-1}$.

EXAMPLE 113

A solution of 280 mg of 4-tert-butyl-N-[3-(2-tetrahydropyranyloxy-ethoxy)-2-(2-methoxy-phenoxy)-phenyl-]-benzenesulphonamide, and 1.0 of p-toluenesulphonic acid in 20 ml of methanol was held at RT for 90 minutes. In order to isolate the product, the solution was evaporated in vac., the residue was partitioned between methylene chloride and saturated sodium bicarbonate solution and the organic phase was dried and evaporated in vac. The residue was recrystallized from acetone-hexane. There were obtained 170 mg of pure 4-tert-butyl-N-[3-(2-hydroxy-ethox)-2-(2-methoxy-phenoxy)-phenyl-benzenesulphonamide, m.p. 131–132° C.

IR spectrum: bands at 3496, 2967, 1507, 1499, 1335, 1168, 750 cm$^{-1}$.

The starting material was prepared as follows:

1.42 g of 2-chloro-3-(2-tetrahydropyranyloxy-ethoxy)-nitrobenzene were heated to 100° C. for 12 hours with 188 mg of sodium hydroxide, 700 mg of guaiacol and 200 mg of copper powder in 15 ml of DMSO. Usual working up and chromatography gave 1.0 g of pure 2-(2-methoxyphenoxy)-3-(2-tetrahydropyranyloxy-ethox)-nitrobenzene, MS spectrum: M$^{t/}$e=359. Catalytic reduction with hydrogen/Raney-nickel in ethanol gave 2-(2-methoxy-phenoxy)-3-(2-tetrahydro-pyranyloxy-ethoxy)-aniline, IR bands at 3369, 2942, 1623, 1327, 870 cm$^{-1}$.

Reaction with p-tert-butylbenzenesulphonyl chloride in pyridine/toluene at room temperature yielded pure 4-tert-butyl-N-[3-(2-tetrahydropyranyloxyethoxy)-2-methoxy-phenoxy)-phenyl]-benzenesulphonamide. MS: M$^{t/}$e=555.

EXAMPLE 114

Analogously to Example 111, from 4-tert-butyl-N-(3-(2-hydroxy-ethoxy)-2-(2-methoxy-phenoxy)-phenyl-benzenesulphonamide there was obtained pure pyridin-2-ylcarbamic acid 2-[3-(4-tert-butyl-phenylsulphonylamino)-2-(2-methoxy-phoxy)-phenoxy]ethyl ester.

M.p. 118–119° C. (acetone/hexane). IR spectrum: bands at 2964, 1733, 1594, 1498, 1254, 769 cm$^{-1}$.

EXAMPLE 115

A solution of 250 mg of 2-(2-methoxy-phenoxy)-3-(2-tetrahydropyranyloxy-ethoxy)-aniline, 183 mg of 5-isopropyl-pyridine-2-sulphonyl chloride, 7 ml of pyridine and 4 ml of toluene was stirred at RT for 4 hours. Usual working up gave 335 mg of oil which was dissolved in 20 ml of methanol and held at RT with 1.0 g of p-toluenesulphonic acid for 1 hour. Usual working up gave 250 mg of pure 5-isopropyl-N-[3-(2-hydroxy-ethoxy)-2-(2-methoxy-phenoxy)-phenyl-pyridyl-sulphonamide, amorphous.

IR spectrum: bands at 2931,1602, 1339,1175, 1021, 764 cm$^{-1}$.

EXAMPLE 116

Analogously to Example 111, from 5-isopropyl-N-[3-(2-hydroxy-ethoxy)-2-(2-methoxy-phenoxy)-phenyl-2-pyridyl-sulphonamide there was obtained pure pyridin-2-yl carbamic acid 2-[3-(5-isopropyl-2-pyridylsulphonylamino)-2-(2-methoxy-phenoxy)ethyl ester.

M.p. 163° C. (acetone-hexane); IR spectrum: bands at 2963, 1732, 1591, 1500, 1304, 1253, 1034, 748 cm$^{-1}$

EXAMPLE 117

Analogously to Example 111, from 2-(2-chloro-5-methoxy-phenoxy)-3-(2-tetrahydropyranyloxy-ethoxy)-aniline with 4-tert-butylbenzenesulphonyl chloride and acidic saponification there was obtained 4-tert-butyl-N-[2-(2-chloro-5-methoxy-phenoxy)-3-(2-hydroxy-ethoxy)-phenyl]benezesulphonamide. M.p. 131–134° C.

The starting material was obtained according to Example 113 from 2-chloro-3-(2-tetrahydropyranyloxy-ethoxy)-nitrobenzene with 2-chloro-5-methoxy-phenol and subsequent reduction of the nitro group.

IR spectrum: bands at 2942, 1600, 1484, 1269, 1205, 1136, 747 cm$^{-1}$.

EXAMPLE 118

Analogously to Example 111, from 4-tert-butyl-N-[2-(2-chloro-5-methoxy-phenoxy)-3-(2-hydroxy-ethoxy)-phenyl]-benzenesulphonamide there was obtained pure pyridin-2-yl-carbamic acid 2-[3-(4-tert-butyl-phenylsulphonylamino)-2-(2-chloro-5-methoxy-phenoxy)-ethyl ester.

M.p. 204–206° C. (methylene chloride/hexane).

EXAMPLE 119 a) 0.14 g of methyl 3-amino-5-(2,3-dihydroxy-propoxy)-4-(3-methoxy-phenoxy)-benzoate was dissolved in pyridine (4.5 ml), treated dropwise while cooling with ice with a solution of 0.16 g of 4-tert-butylbenzenesulphonyl chloride in toluene (1.5 ml) and subsequently stirred at room temperature for 5 hours. The reaction mixture was partitioned between water and ethyl acetate and the organic phase was washed with 2N HCl solution and dried over magnesium sulphate. After removing the solvent the residue was chromatographed over silica gel with methylene chloride/methanol (40/1) as the eluent. There were thus obtained 121 mg of methyl 3-(4-tert-butylbenzenesulphonylamino)-5-(2, 3-dihydroxy-propoxy)-4-(3-methoxy-phenoxy)-benzoate as a resin.

MS: 558.2 (M–H).

Preparation of the Starting Material:

b) 3.67 g of methyl 4-chloro-3-hydroxy-5-nitro-benzoate were dissolved in acetone (100 ml), treated in succession at room temperature with 6.57 g of potassium carbonate and 2.68 ml of allyl bromide and the mixture was heated at reflux for 17 hours. Subsequently, the reaction mixture was diluted with ethyl acetate, poured into water and the organic phase was isolated, dried over sodium sulphate and concentrated on a rotary evaporator. There was thus obtained methyl 3-allyloxy-4-chloro-5-nitro-benzoate as a crystalline solid.

MS: 231 (M).

c) 5.3 g of methyl 3-allyloxy-4-chloro-5-nitro-benzoate were dissolved in acetone (100 ml), treated at room temperature with 6.57 g of potassium carbonate and 3.66 g of 3-methoxyphenol and the mixture was heated at reflux for 24 hours. The mixture was poured into ice-water and extracted with ethyl acetate. The organic phase was washed 3 times with 5% sodium hydroxide solution and then with water, dried over sodium sulphate and finally concentrated on a rotary evaporator. The crude product (6.2 g) was chromatographed on silica gel with hexane/ether (3/1). There was thus obtained methyl 3-allyloxy-4-(3-methoxy-phenoxy)-5-nitro-benzoate as a lemon-yellow, crystalline solid.

MS: 359 (M).

d) 0.35 g of methyl 3-allyloxy-4-(3-methoxy-phenoxy)-5-nitro-benzoate was dissolved in acetone/water (5 ml) and treated at room temperature with 4-methylmorpholine 4-N-oxide (0.165 9) and subsequently with osmium tetroxide (1 mg) dissolved in 1 ml of dist. water. The mixture was stirred at room temperature for 3 hours, treated with sodium pyrosulphite (0.17 g) and stirred at room temperature for a further hour. The resulting brown precipitate was filtered off over Dicalite and rinsed with acetone. The filtrate was concentrated on a rotary evaporator and the residue was taken up in ethyl acetate and washed with aqueous 1N HCl and then with water. After drying the organic phase over magnesium sulphate it was concentrated on a rotary evaporator and the residue was chromatographed over silica gel with methylene chloride/methanol (30/1) as the eluent. There was thus obtained methyl 3-(2,3-dihydroxy-propoxy)-4-(3-methoxy-phenoxy)-5-nitro-benzoate as a resin.

MS: 393 (M).

e) 0.33 g of methyl 3-(2,3-dihydroxy-propoxy)-4-(3-methoxy-phenoxy)-5-nitro-benzoate was dissolved in methanol (10 ml), treated with Ra-Ni catalyst and hydrogenated at room temperature for 1 hour. The catalyst was filtered off and the solution was concentrated on a rotary evaporator. There was thus obtained methyl 3-amino-5-(2,3-dihydroxy-propoxy)-4-(3-methoxy-phenoxy)-benzoate, pale yellow crystalline solid.

MS: 364 (M+H).

EXAMPLE 120

0.15 g of methyl 3-(4-tert-butyl-benzenesulphonylamino)-5-(2,3-dihydroxypropoxy)-4-(3-methoxy-phenoxy)-benzoate was dissolved in methanol (8 ml), treated with 1.6 ml of 1 N NaOH solution and subsequently heated under reflux for 16 hours. The mixture was poured on to ice-water, acidified with dilute HCl solution to pH 1 and the product was extracted with ethyl acetate. The organic phase was dried over sodium sulphate, concentrated and the solid obtained was dried in a high vacuum. There was thus obtained 3-(4-tert-butyl-benzenesulphonylamino)-5-(2,3-dihydroxy-propoxy)-4-(3-methoxy-phenoxy)-benzoic acid as a white foam.

MS: 544.2 (M–H).

EXAMPLE 121

54 mg of 3-(4-tert-butyl-benzenesulphonylamino)-5-(2,3-dihydroxy-propoxy)-4-(3-methoxy-phenoxy)-benzoic acid were dissolved in methylene chloride (5 ml), 40 µl of N-ethyldiisopropylamine, 30 mg of bis-(2-oxo-oxazolidinyl)-phosphinic acid chloride and 11 µl of aniline were added thereto in succession at room temperature and the mixture was subsequently stirred at room temperature for 12 hours. The mixture was taken up in ethyl acetate, subsequently washed firstly with water and then with 1 N aqueous HCl and the organic phase was dried over sodium sulphate and concentrated on a rotary evaporator. The residue was chromatographed over silical gel with CH$_2$Cl$_2$/MeOH (30/1) as the eluent. There was thus obtained 3-(4-tert-butyl-benzenesulphonylamino)-5-(2,3-dihydroxy-propoxy)-4-(3-methoxy-phenoxy)-N-phenyl-benzamide as a white foam.

MS: 619.3 (M–H).

EXAMPLE 122

In analogy to Example 119, from methyl 3-amino-5-(2,3-dihydroxy-propoxy)-4-(3-methoxy-phenoxy)-benzoate and 4-methoxybenzenesulphonyl chloride there was obtained methyl 3-(2,3-dihydroxy-propoxy)-5-(4-methoxy-benzenesulphonylamino)-4-(3-methoxy-phenoxy)-benzoate as a resin.

MS: 532.1 (M–H).

EXAMPLE 123

In analogy to Example 120, by acid saponification of methyl 3-(2,3-dihydroxy-propoxy)-5-(4-methoxy-benzenesulphonylamino)-4-(3-methoxy-phenoxy)-benzoate there was obtained 3-(2,3-dihydroxy-propoxy)-5-(4-methoxy-benzenesulphonylamino)-4-(3-methoxy-phenoxy)-benzoic acid, white foam.

MS: 518 (M–H).

EXAMPLE 124

In analogy to Example 121, by coupling 3-(2,3-dihydroxy-propoxy)-5-(4-methoxy-benzenesulphonylamino)-4-(3-methoxy-phenoxy)-benzoic acid with aniline there was obtained 3-(2,3-dihydroxy-propoxy)-5-(4-methoxy-benzenesulphonylamino)-4-(3-methoxy-phenoxy)-N-phenyl-benzamide as a foam.

MS: 593.2 (M–H).

EXAMPLE 125

In analogy to Example 119, from methyl 3-amino-5-(2,3-dihydroxy-propoxy)-4-(3-methoxy-phenoxy)-benzoate and 4-methyl-mercaptobenzeneolsulphonyl chloride there was obtained methyl 3-(2,3-dihydroxy-propoxy)-4-(3-methoxy-phenoxy)-5-(4-methylsulphanyl-benzenesulphonylamino)-benzoate as a foam.

MS: 548.1 (M–H).

EXAMPLE 126

In analogy to Example 120, by acid saponification of methyl 3-(2,3-dihydroxy-propoxy)-4-(3-methoxy-phenoxy)-5-(4-methylsulphanybenzenesulphonylamino)-benzoate there was obtained 3-(2,3-dihydroxy-propoxy)-4-(3-methoxy-phenoxy)-5-(4-methylsulphanyl-benzenesulphonylamino)-benzoic acid as a white solid.

MS: 534.1 (M–H).

EXAMPLE 127

In analogy to Example 121, by coupling 3-(2,3-dihydroxy-propoxy)-4-(3-methoxy-phenoxy)-5-(4-methylsulphanyl-benzenesulphonylamino)-benzoic acid with aniline there was obtained 3-(2,3-dihydroxy-propoxy)-4-(3-methoxy-phenoxy)-5-(4-methylsulphanyl-benzenesulphonylamino)-N-phenyl-benzamide as a foam.

MS: 609.1 (M–H).

EXAMPLE 128

In analogy to Example 121, by coupling 3-(4-tert-butyl-benzenesulphonylamino)-5-(2,3-dihydroxy-propoxy)-4-(3-methoxy-phenoxy)-benzoic acid with 5-aminotetrazole there was obtained 3-(44ert-butybenzenesulphonylamino)-5-(2,3-dihydroxy-propoxy)-4-(3-methoxy-phenoxy)-N-(1H-tetrazol-5-yl)-benzamide as a white solid.

MS: 543.2 (M-CHN4-H).

EXAMPLE 129

In analogy to Example 121, by coupling 3-(2,3-dihydroxy-propoxy)-4-(3-methoxy-phenoxy)-5-(4- methylsulphanyl-benzenesulphonylamino)-benzoic acid with 1-acetoxycarbonylpiperazine there was obtained ethyl 4-[3-(2,3-dihydroxy-propoxy)-4-(3-methoxy-phenoxy)-5-(4-methylsulphanylbenzenesulphonylamino)-benzoyl]-piperazine-1-carboxylate as a white foam.

MS: 674.3 (M−H).

EXAMPLE 130

In analogy to Example 121, by coupling 3-(2,3-dihydroxy-propoxy)-4-(3-methoxy-phenoxy)-5-(4-methylsulphanyl-benzenesulphonylamino)-benzoic acid with morpholine there was obtained N-[3-(2,3-dihydroxy-propoxy)-2-(3-methoxy-phenoxy)-5-(morpholine-4-carbonyl)-phenyl]-4 methylsulphanyl-benzenesulphonamide as a white foam.

MS: 603.3 (M−H).

EXAMPLE 131

Methyl 3-(4-tert-butyl-phenylsulphonyl-amino)-5-(2-hydroxy-ethoxy)-4-(2-methoxy-phenoxy)-benzoate (132 mg) was dissolved in N,N-dimethylacetamide (2.5 ml), 30 mg of 60% NaH suspension were added thereto at room temperature and the mixture was stirred at room temperature for 20 minutes and finally treated with 2-chloropyrimidine (40 mg). The reaction mixture was stirred at room temperature for 18 hours, poured on to ice-water, saturated NH$_4$Cl solution was added and the mixture was extracted with ethyl acetate. The organic phase was washed with water, dried over magnesium sulphate and finally concentrated on a rotary evaporator. The residue was chromatographed over silica gel with methylene chloride/ethyl acetate (7/1) as the eluent. There was thus obtained methyl 3-(4-tert-butyl-benzenesulphonylamino)-4-(2-methoxy-phenoxy)-5-[2-(pyrimidin-2-yloxy)-ethoxy]-benzoate as a foam.

MS: 608.2 (M+H).

EXAMPLE 132

In analogy to Example 131, from 4-tert-butyl-N-[3-(2-hydroxy-ethoxy)-2-(2-methoxy-phenoxy)-5-(morpholine-4-carbonyl)-phenyl]-benzenesulphonamide and 2-chloropyrimidine there was obtained 4-tert-butyl-N-{2-(2-methoxy-phenoxy)-5-(morpholine-4-carbonyl)-3-[2-(pyrimidin-2-yloxy)-ethoxy]-phenyl}-benzenesulphonamide as a white foam.

MS: 661.3 (M−H).

EXAMPLE 133

In analogy to Example 131, from 4-tert-butyl-N-[3-(2-hydroxy-ethoxy)-2-(2-methoxy-phenoxy)-5-(morpholine-4-carbonyl)-phenyl]-benzenesulphonamide and 2-chloropyridine there was obtained 4-tert-butyl-N-{2-(2-methoxy-phenoxy)-5-(morpholin-4-carbonyl)-3-[2-(pyridin-2-yloxy)-ethoxy]-phenyl}-benzenesulphonamide as a foam.

MS: 660.3 (M−H).

EXAMPLE 134

In analogy to Example 131, from 3-(2-hydroxy-ethoxy)-4-(3-methoxy-phenoxy)-5-(4-methylsulphanyl-benzenesulphonyl-amino)-N-phenyl-benzamide and 2-chloropyrimidine there was obtained 4-(3-methoxy-phenoxy)-3-(4-methylsulphanyl-benzenesulphonylamino)-N-phenyl-5-[2-(pyrimidin-2-yloxy)-ethoxy]-benzamide as a solid.

MS: 657.4 (M−H).

EXAMPLE 135

In analogy to Example 131, from 3-(2-hydroxy-ethoxy)-4-(3-methoxy-phenoxy)-5-(4-methylsulphanyl-benzenesulphonyl-amino)-N-phenyl-benzamide and 2-chloropyridine there was obtained 4-(3-methoxy-phenoxy)-3-(4-methylsulphanyl-benzenesulphonylamino)-N-phenyl-5-[2-(pyridin-2-yloxy)-ethoxy]-benzamide as a solid.

MS: 656.3 (M−H).

EXAMPLE 136

In analogy to Example 121, by coupling 3-(2-hydroxy-ethoxy)-4-(3-methoxy-phenoxy)-5-(4-methylsulphanyl-benzenesulphonylamino)-benzoic acid with morpholine there was obtained N-[3-(2-hydroxy-ethoxy)-2-(3-methoxy-phenoxy)-5-(morpholine-4-carbonyl)-phenyl]-4-methylsulphanyl-benzenesulphonamide.

MS: 575 (M+H).

EXAMPLE 137

In analogy to Example 131, from N-[3-(2-hydroxy-ethoxy)-2-(3-methoxy-phenoxy)-5-(morpholine-4-carbonyl)-phenyl]-4-methylsulphanyl-benzenesulphonamide and 2-chloropyrimidine there was obtained N-2-(3-methoxy-phenoxy)-5-(morpholine-4-carbonyl)-3-[2-(pyrimidin-2-yloxy)-ethoxy]-phenyl)-4-methylsulphanyl-benzenesulphonamide as a foam.

MS: 651.3 (M−H).

EXAMPLE 138

In analogy to Example 131, from N-[3-(2-hydroxy-ethoxy)-2-(3-methoxy-phenoxy)-5-(morpholine-4-carbonyl)-phenyl]-4-methylsulphanyl-benzenesulphonamide and 2-chloropyridine there was obtained N-{2-(3-methoxy-phenoxy)-5-(morpholine-4-carbonyl)-3-[2-(pyridin-2-yloxy)-ethoxy]-phenyl}4-methylsulphanyl-benzenesulphonamide as a foam.

MS: 650.3 (M−H).

EXAMPLE 139 a) 2.2 g of 3-amino-5-(2-hydroxy-ethoxy)-4-(2-methoxy-phenoxy)-benzonitrile were dissolved in pyridine (45 ml), treated dropwise while cooling with ice with a solution of 3.06 g of 4-tert-butylbenzenesulphonyl chloride in toluene (15 ml) and subsequently stirred at room temperature for 12 hours. The reaction solution was partitioned between aqueous hydrochloric acid (pH 1) and ethyl acetate and the organic phase was dried over magnesium sulphate. After removing the solvent on a rotary evaporator the crude product was chromatographed over silica gel with methylene chloride/ethyl acetate (8/1) as the eluent. There were thus obtained 1.19 g of 4-tert-butyl-N-[5-cyano-3-(2-hydroxy-ethoxy)-2-(2-methoxy-phenoxy)-phenyl]-benzenesulphonamide as a foam.

MS: 495.1 (M−H).

Preparation of the Starting Material:

b) In order to prepare a Vilsmeyer complex, DMF (11.5 ml) was placed at −20° C., 12.9 ml of oxalyl chloride were cautiously added dropwise at the same temperature and the mixture was left to react at −20° C. for 10 minutes. Subsequently, a solution of 9 g of 3,4-dihydroxy-5-nitrobenzonitrile (preparation described in: J. Med. Chem.

849,1989) in DMF (11.5 ml) was slowly added dropwise thereto, with the temperature of the reaction solution being held at between −10° C. and −20° C. The mixture was left to come to room temperature and was subsequently heated on an oil bath at 100° C. (bath temperature) for a further 5 hours. The dark reaction solution was poured on to ice-water, extracted with ethyl acetate and the organic phase was washed three times with water, dried over sodium sulphate and concentrated on a rotary evaporator. There was thus obtained 4-chloro-3-hydroxy-5-nitro-benzonitrile as a beige powder which was used in the next step without further purification.

MS: 197.1 (M−H).

c) 3.96 g of 4-chloro-3-hydroxy-5-nitro-benzonitrile were dissolved in acetone (150 ml), treated in succession at room temperature with 6.91 g of potassium carbonate and 7.68 g of 2-(2-iodo-ethoxy)-tetrahydro-pyran and the mixture was heated at reflux for 22 hours. Subsequently, it was poured into water, extracted with ethyl acetate and the organic phase was dried over sodium sulphate and concentrated on a rotary evaporator. The residue was flash chromatographed on silica gel with hexane/ethyl acetate (3/1) as the eluent. There was thus obtained 4-chloro-3-nitro-5-[2-(tetrahydro-pyran-2-yloxy)-ethoxy]-benzonitrile as a pale yellow resin.

MS: 326 (M).

d) 2.60 g of 4-chloro-3-nitro-5-[2-(tetrahydro-pyran-2-yloxy)-ethoxy]-benzonitrile were dissolved in acetone (75 ml), treated at room temperature with 3.3 g of potassium carbonate and 1.48 g of guaiacol and the mixture was heated at reflux for 20 hours. The mixture was poured on to ice-water and extracted with ethyl acetate. The organic phase was washed 3 times with 5% sodium hydroxide solution and then with water, dried over sodium sulphate and finally concentrated on a rotary evaporator. The crude product was flash chromatographed on silica gel with hexane-ethyl acetate (2/1). There was thus obtained 4-(2-methoxy-phenoxy)-3-nitro-5-[2-(tetrahydro-pyran-2-yloxy)-ethoxy]-benzonitrile as a yellow resin.

MS: 414 (M).

e) 3.5 g of 4-(2-methoxy-phenoxy)-3-nitro-5-[2-(tetrahydro-pyran-2-yloxy)-ethoxy]-benzonitrile were dissolved in ethanol (100 ml), a solution of tin dichloride dihydrate (7.6 g) in 37% HCl (17 ml) was added dropwise thereto at room temperature and the mixture was subsequently stirred at room temperature for 12 hours. The mixture was poured on to ice-water, adjusted to pH 7 and the product was extracted with ethyl acetate. After usual processing of the organic phase there was obtained 3-amino-5-(2-hydroxy-ethoxy)-4-(2-methoxy-phenoxy)-benzonitrile as a crystalline solid.

MS: 300 (M).

EXAMPLE 140

4-tert-Butyl-N-[5-cyano-3-(2-hydroxy-ethoxy)-2-(2-methoxy-phenoxy)-phenyl]-benzenesulphonamide (124 mg) was dissolved in N,N-dimethylformamide, treated at room temperature with ammonium chloride (134 mg) followed by sodium azide (162 mg) and the mixture was subsequently heated at 70° C. for 24 hours. The N,N-dimethylformamide was removed in a high vacuum, the residue was partitioned between water/ethyl acetate and the organic phase was washed several times with saturated sodium chloride solution, finally dried over magnesium sulphate and evaporated on a rotary evaporator. The crude product was purified on silica gel with methylene chloride/ methanol (5/1) as the eluent. There was thus obtained 4-tert-butyl-N-[3-(2-hydroxy-ethoxy)-2-(2-methoxy-phenoxy)-5-(1 H-tetrazol-5-yl)-phenyl]-benzenesulphonamide as a white foam.

MS: 538.1 (M−H).

EXAMPLE 141 a) 0.89 g of 3-amino-5-(2-hydroxy-ethoxy)-4-(3-methoxy-phenoxy)-benzonitrile was dissolved in pyridine (15 ml), treated dropwise while cooling with ice with a solution of 1.23 g of 4-tert-butylbenzenesulphonyl chloride in toluene (5 ml) and subsequently stirred at room temperature for 12 hours. The reaction solution was partitioned between aqueous acid (pH 1) and ethyl acetate and the organic phase was dried over magnesium sulphate. After removing the solvent on a rotary evaporator the crude product was chromatographed over silica gel with methylene chloride/ethyl acetate (5/1) as the eluent. There was thus obtained 0.61 g of 4-tert-butyl-N-[5-cyano-3-(2-hydroxy-ethoxy)-2-(3-methoxy-phenoxy)-phenyl]-benzene-sulphonamide as a white solid.

MS: 495.2 (M−H).

Preparation or the Starting Material:

b) 2.57 g of 4-chloro-3-nitro-5-[2-(tetrahydro-pyran-2-yloxy)-ethoxy]-benzonitrile were dissolved in acetone (100 ml), treated at room temperature with 3.24 g of potassium carbonate and 1.48 g of resorcinol monomethyl ether and the mixture was heated at reflux for 20 hours. The mixture was poured on to ice-water and extracted with ethyl acetate. The organic phase was washed 3 times with 5% sodium hydroxide solution and then with water, dried over sodium sulphate and finally concentrated on a rotary evaporator. The crude product was flash chromatographed on silica gel with hexane/ethyl acetate (2/1). There was thus obtained 4-(3-methoxy-phenoxy)-3-nitro-5-[2-(tetrahydro-pyran-2-yloxy)-ethoxy]-benzonitrile as a crystalline solid.

c) 2.0 g of 4-(3-methoxy-phenoxy)-3-nitro-5-[2-(tetrahydro-pyran-2-yloxy)-ethoxy]-benzonitrile were dissolved in ethanol (60 ml), a solution of tin dichloride dihydrate (4.5 g) in 37% HCl (12 ml) was added dropwise thereto at room temperature and the mixture was subsequently stirred at room temperature for 12 hours. The mixture was poured on to ice-water, adjusted to pH 7 and the product was extracted with ethyl acetate. After usual processing of the organic phase there was obtained 3-amino-5-(2-hydroxy-ethoxy)-4-(3-methoxy-phenoxy)-benzonitrile as a white solid.

MS: 301.2 (M+H).

EXAMPLE 142

In analogy to Example 140, by reacting 4-tert-butyl-N-[5-cyano-3-(2-hydroxy-ethoxy)-2-(3-methoxy-phenoxy)-phenyl]-benzenesulphonamide and sodium azide in N,N-dimethylformamide there was obtained 4-tert-butyl-N-[3-(2-hydroxy-ethoxy)-2-(3-methoxy-phenoxy)-5-(1 H-tetrazol-5-yl)-phenyl]-benzenesulphonamide as a white foam.

MS: 538.2 (M−H).

EXAMPLE 143 a) 0.25 g of N-[3-allyloxy-5-cyano-2-(2-methoxy-phenoxy)-phenyl]-4-tert-butyl-benzenesulphonamide was dissolved in acetone (10 ml) and treated at room temperature with 4-methylmorpholine 4-N-oxide (0.082 g) and subsequently with osmium tetroxide (1 mg) dissolved in 1 ml of dist. water. The mixture was stirred at room temperature for 44 hours, again treated with $OsO_4$ (1 mg in 3 ml of water)

in order to complete the reaction and stirred at room temperature for a further 6 hours. Subsequently, sodium pyrosulphite (0.085 g) was added and the mixture was stirred at room temperature for a further hour. The resulting brown precipitate was filtered off over Dicalite and rinsed with acetone. The filtrate was concentrated on a rotary evaporator and the residue was taken up in ethyl acetate and washed with aqueous 1N HCl and then with water. After drying the organic phase over magnesium sulphate it was concentrated on a rotary evaporator and the residue was chromatographed over silica gel with methylene chloride/methanol (20/1) as the eluent. There was thus obtained 4-tert-butyl-N-[5-cyano-3-(2,3-dihydroxy-propoxy)-2-(2-methoxy-phenoxy)-phenyl]-benzenesulphonamide as a white solid.

MS: 525.1 (M–H).

Preparation of the Starting Material:

b) 1.98 g of 4-chloro-3-hydroxy-5-nitro-benzonitrile were dissolved in acetone (100 ml), treated in succession at room temperature with 4.14 g of potassium carbonate and 1.27 ml of allyl bromide and the mixture was heated at reflux for 20 hours. Subsequently, the reaction mixture was diluted with ethyl acetate, poured into water and the organic phase was isolated, dried over sodium sulphate and concentrated on a rotary evaporator. The residue was chromatographed over silica gel with hexane/ether (4/1) as the eluent. There was thus obtained 3-allyloxy-4-chloro-5-nitro-benzonitrile as a crystalline solid.

MS: 238 (M).

c) 2.27 g of 3-allyloxy-4-chloro-5-nitro-benzonitrile were dissolved in acetone (100 ml), treated at room temperature with 3.94 g of potassium carbonate and 1.76 g of guaiacol and the mixture was heated at reflux for 20 hours. The mixture was poured on to ice-water and extracted with ethyl acetate. The organic phase was washed 3 times with 5% sodium hydroxide solution and then with water, dried over sodium sulphate and finally concentrated on a rotary evaporator. The crude product was chromatographed on silica gel with hexane/ethyl acetate (4/1). There was thus obtained 3-allyloxy-4-(2-methoxy-phenoxy)-5-nitro-benzonitrile as a crystalline solid.

MS: 326 (M).

d) 3.59 g of 3-allyloxy-4-(2-methoxy-phenoxy)-5-nitro-benzonitrile were dissolved in ethanol (120 ml), a solution of tin dichloride dihydrate (8.55 g) in 37% HCl (25 ml) was added dropwise thereto at room temperature and the mixture was subsequently stirred at room temperature for 12 hours. The mixture was poured on to ice-water, adjusted to pH 7 and the product was extracted with ethyl acetate. After usual processing of the organic phase there was obtained 3-allyloxy-5-amino-4-(2-methoxy-phenoxy)-benzonitrile as a white solid.

MS: 296 (M+H).

e) 0.3 g of 3-allyloxy-5-amino-4-(2-methoxy-phenoxy)-benzonitrile was dissolved in pyridine (9 ml), treated dropwise while cooling with ice with a solution of 0.42 g of 4-tert-butylbenzenesulphonyl chloride in toluene (3 ml) and subsequently stirred at room temperature for 12 hours. The reaction solution was partitioned between aqueous acid (pH 1) and ethyl acetate and the organic phase was dried over magnesium sulphate. After removing the solvent on a rotary evaporator the crude product was chromatographed over silica gel with methylene chloride/ethyl acetate (60/1) as the eluent. There was thus obtained 0.61 g of N-[3-allyloxy-5-cyano-2-(2-methoxy-phenoxy)-phenyl]-4-tert-butyl-benzenesulphonamide as a white solid.

MS: 491.2 (M–H).

EXAMPLE 144

4-tert-Butyl-N-[5-cyano-3-(2,3-dihydroxy-propoxy)-2-(2-methoxy-phenoxy)-phenyl]-benzenesulphonamide (131 mg) was dissolved in N,N-dimethylformamide (2.5 ml), treated at room temperature with ammonium chloride (134 mg) followed by sodium azide (162 mg) and the mixture was subsequently heated at 70° C. for 24 hours. Additional sodium azide (162 mg) was added and the mixture was stirred at 70° C. for a further 16 hours. The N,N-dimethylformamide was removed in a high vacuum, the residue was partitioned between water/ethyl acetate and the organic phase was washed several times with saturated sodium chloride solution, finally dried over magnesium sulphate and evaporated on a rotary evaporator. The crude product was purified on silica gel with methylene chloride/methanol (3/1) as the eluent. There was thus obtained 4-tert-butyl-N-[3-(2,3-dihydroxy-propoxy)-2-(2-methoxy-phenoxy)-5-(1H-tetrazol-5-yl)-phenyl]-benzenesulphonamide as a white foam.

MS: 568.3 (M–H).

EXAMPLE 145 a) Analogously to Example 143, by oxidizing N-[3-allyloxy-5-cyano-2-(3-methoxy-phenoxy)-phenyl]-4-tert-butyl-benzenesulphonamide with osmium tetroxide there was obtained 4-tert-butyl-N-[5-cyano-3-(2,3-dihydroxy-propoxy)-2-(3-methoxy-phenoxy)-phenyl]-benzenesulphonamide as a solid.

MS: 525.1 (M–H).

Preparation of the Starting Material:

b) Analogously to Example 143c), from 3-allyloxy-4-chloro-5-nitro-benzonitrile and resorcinol monomethyl ether there was obtained 3-allyloxy-4-(3-methoxy-phenoxy)-5-nitro-benzonitrile.

MS: 326 (M).

c) Analogously to Example 143d), from 3-allyloxy-4-(3-methoxy-phenoxy)-5-nitro-benzonitrile there was obtained by reduction 3-allyloxy-5-amino-4-(3-methoxy-phenoxy)-benzonitrile as a crystalline solid.

MS: 296 (M+H).

d) Analogously to Example 143e), from 3-allyloxy-5-amino-4-(3-methoxy-phenoxy)-benzonitrile by coupling with 4-tert-butylbenzenesulphonyl chloride there was obtained N-[3-allyloxy-5-cyano-2-(3-methoxy-phenoxy)-phenyl]-4-tert-butyl-benzenesulphonamide as a crystalline solid.

MS: 491.2 (M–H).

EXAMPLE 146

Analogously to Example 144, from 4-tert-butyl-N-[5-cyano-3-(2,3-dihydroxy-propoxy)-2-(3-methoxy-phenoxy)-phenyl]-benzenesulphonamide by cyclization with sodium azide in N,N-dimethylformamide as the solvent there was obtained 4-tert-butyl-N-[3-(2,3-dihydroxy-propoxy)-2-(3-methoxy-phenoxy)-5-(1H-tetrazol-5-yl)-phenyl]-benzenesulphonamide as a crystalline solid.

MS: 568.3 (M–H).

Example A

Tablets containing the following ingredients can be produced in a conventional manner:

| Ingredients | Per tablet |
| --- | --- |
| Compound of formula I | 10.0–100.0 mg |
| Lactose | 125.0 mg |
| Corn starch | 75.0 mg |
| Talc | 4.0 mg |
| Magnesium stearate | 1.0 mg |

Example B

Capsules containing the following ingredients can be produced in a conventional manner:

| Ingredients | Per capsule |
| --- | --- |
| Compound of formula I | 25.0 |
| Lactose | 150.0 mg |
| Corn starch | 20.0 mg |
| Talc | 5.0 mg |

Example C

Injection solutions can have the following composition:

| Compound of formula I | 3.0 |
| --- | --- |
| Gelatine | 150.0 mg |
| Phenol | 4.7 mg |
| Water for injection solutions | ad 1.0 mg |

Example D 500 mg of compound of formula I are suspended in 3.5 ml of Myglyol 812 and 0.08 g of benzyl alcohol. This suspension is filled into a container having a dosage valve. 5.0 g of Freon 12 are filled into the container under pressure through the valve. The Freon is dissolved in the Myglyol-benzyl alcohol mixture by shaking. This spray container contains about 100 single doses, which can be applied individually.

What is claimed is:

1. A compound of formula:

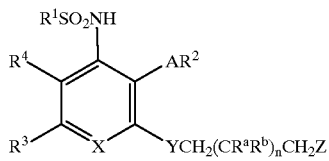

I wherein $R^1$ is phenyl, substituted phenyl or heterocyclyl;

$R^2$ is phenyl or substituted phenyl;

$R^3$ is hydrogen, lower-alkyl, cyano, carboxy, esterified carboxy, phenyl, substituted phenyl, heterocyclyl or a residue —$CONR^5R^6$ or —$NR^5COR^7$;

$R^4$ is hydrogen or lower-alkyl;

$R^5$ is hydrogen or a residue $R^7$, and $R^6$ is —$(CH_2)_m R^7$; or $R^5$ and $R^6$ together with the N atom associated with them is a heterocyclic residue;

$R^7$ is phenyl, substituted phenyl, cycloalkyl, heterocyclyl, lower-alkyl, cyano-lower-alkyl, hydroxy-lower-alkyl, di-lower-alkylamino-lower-alkyl, carboxy-lower-alkyl, lower-alkoxycarbonyl-lower-alkyl, lower-alkoxycarbonylamino-lower-alkyl or phenyl-lower-alkoxycarbonyl;

$R^a$ is hydrogen, lower-alkyl or hydroxy;

$R^b$ is hydrogen or lower-alkyl;

Z is hydroxy, amino or a residue —$OR^8$, —$OC(O)NHR^8$, —$OC(O)OR^8$, —$NHC(O)NHR^8$ or —$NHC(O)OR^8$;

$R^8$ is heterocyclyl, phenyl, substituted phenyl or lower-alkyl;

A and Y each independently is oxygen or sulphur,

X is nitrogen;

m is 0, 1 or 2; and n is 0, 1 or 2;

or a pharmaceutically usable salt thereof.

2. The compound according to claim 1, wherein $R^1$ is phenyl or substituted phenyl.

3. The compound according to claim 2, wherein Z is —$OC(O)NHR^8$.

4. The compound according to claim 2, wherein Z is hydroxy.

5. The compound according to claim 3 which is pyridin-2-yl-carbamic acid 2[4(4-tert-butyl-benzenesulphonamino)-3-(2-methoxyphenoxy)-6-phenyl-pyridin-2-yloxy]-ethyl ester.

6. The compound according to claim 4 which is p-tert-butyl-N-[2-(2-hydroxyethoxy)-3-(o-methoxyphenoxy)-6-methyl-4-pyridyl-]benzenesulphonamide.

7. The compound according to claim 4 which is p-tert-butyl-N-[2-(2-hydroxyethoxy)-3-(3-methoxy-phenoxy)-6-methyl-4-pyridyl]benzenesulphonamide.

8. The compound according to claim 4 which is 4-tert-butyl-N-[2-(2-hydroxyethoxy)-3-(2-methoxyphenoxy)-6-phenyl-pyrid-4-yl]-benzenesulphonamide.

9. The compound according to claim 2, wherein $R^1$ is heterocyclyl.

10. The compound according to claim 9, wherein Z is —$OC(O)NHR^8$.

11. The compound according to claim 9, wherein Z is hydroxy.

12. The compound according to claim 10 which is pyridin-2-yl-carbamic acid-2-[4-(5-isopropyl-pyridine-2-sulphonylamino)-3-(2-methoxy-phenoxy)-6-methyl-pyridin-2-yloxy]-ethyl ester.

13. The compound according to claim 11 which is N-[2-(2-hydroxyethoxy)-3-(2-methoxyphenoxy)-6-methyl-pyridin-4-yl]-5-isopropyl-pyridine-2-sulphonamide.

14. The compound according to claim 1, wherein Z is $OR^8$.

15. The compound methyl 3-(4-tert-butyl-benzenesulphonylamino)-4-(2-methoxy-phenoxy)-5-[2-(pyrimidin-2-yloxy)-ethoxy]-benzoate or a pharmaceutically usable salt thereof.

16. The compound 4-tert-butyl-N-{2-(2-methoxy-phenoxy)-5-(morpholine-4-carbonyl)-3-[2-(pyrimidin-2-yloxy)-ethoxy]-phenyl}-benzenesulphonamide or a pharmaceutically usable salt thereof.

17. The compound 4-tert-butyl-N-{2-(2-methoxy-phenoxy)-5-(morpholine-4-carbonyl)-3-[2-(pyridin-2-yloxy)-ethoxy]-phenyl}-benzenesulphonamide or a pharmaceutically usable salt thereof.

18. The compound 4-(3-methoxy-phenoxy)-3-(4-methylsulphanyl-benzenesulphonylamino)-N-phenyl-5-[2-(pyrimidin-2-yloxy)-ethoxy]-benzamide or a pharmaceutically usable salt thereof.

19. The compound 4-(3-methoxy-phenoxy)-3-(4-methylsulphanyl-benzenesulphonylamino)-N-phenyl-5-[2-(pyridin-2-yloxy)-ethoxy]-benzamide or a pharmaceutically usable salt thereof.

20. The compound N-{2-(3-methoxy-phenoxy)-5-(morpholine-4-carbonyl)-3-[2-(pyrimidin-2-yloxy)-ethoxy]-phenyl}-4-methylsulphanyl-benzenesulphonamide or a pharmaceutically usable salt thereof.

21. The compound N-{2-(3-methoxy-phenoxy)-5-(morpholine-4-carbonyl)-3-[2-(pyridin-2-yloxy)-ethoxy]-phenyl}-4-methylsulphanyl-benzenesulphonamide or a pharmaceutically usable salt thereof.

22. A process for making a compound of the formula:

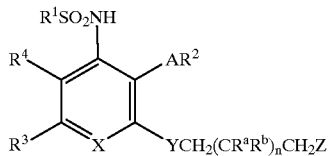
I wherein
$R^1$ is phenyl, substituted phenyl or heterocyclyl;
$R^2$ is phenyl or substituted phenyl;
$R^3$ is hydrogen, lower-alkyl, cyano, carboxy, esterified carboxy, phenyl, substituted phenyl, heterocyclyl or a residue —$CONR^5R^6$ or —$NR^5COR^7$;
$R^4$ is hydrogen or lower-alkyl;
$R^5$ is hydrogen or a residue $R^7$, and
$R^6$ is —$(CH_2)_m R^7$; or
$R^5$ and $R^6$ together with the N atom associated with them is a heterocyclic residue;
$R^7$ is phenyl, substituted phenyl, cycloalkyl, heterocyclyl, lower-alkyl, cyano-lower-alkyl, hydroxy-lower-alkyl, di-lower-alkylamino-lower-alkyl, carboxy-lower-alkyl, lower-alkoxycarbonyl-lower-alkyl, lower-alkoxycarbonylamino-lower-alkyl or phenyl-lower-alkoxycarbonyl;
$R^a$ is hydrogen, lower-alkyl or hydroxy;
$R^b$ is hydrogen or lower-alkyl;
Z is hydroxy, amino or a residue —$OR^8$, —$OC(O)NHR^8$, —$OC(O)OR^8$, —$NHC(O)NHR^8$ or —$NHC(O)OR^8$;
$R^8$ is heterocyclyl, phenyl, substituted phenyl or lower-alkyl;
A and Y each independently is oxygen or sulphur,
X is nitrogen or CH;
m is 0, 1 or 2; and
n is 0, 1 or 2;
or a pharmaceutically usable salt thereof,
which process comprises reacting a compound of the formula

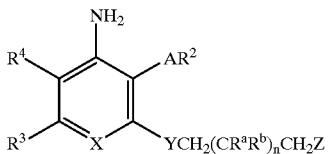
II wherein $R^2, R^3, R^4, R^a, R^b, A, X, Y, Z$ and n have the significance given above and amino or hydroxy groups optionally contained in $R^3$ and Z are present in protected form, with a reactive derivative of a sulphonic acid of the formula $R^1SO_2OH$.

23. A process for making a compound of the formula,

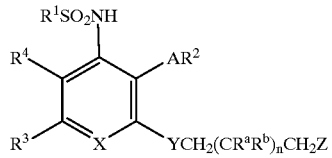
I wherein
$R^1$ is phenyl, substituted phenyl or heterocyclyl;
$R^2$ is phenyl or substituted phenyl;
$R^3$ is hydrogen, lower-alkyl, cyano, carboxy, esterified carboxy, phenyl, substituted phenyl, heterocyclyl or a residue —$CONR^5R^6$ or —$NR^5COR^7$;
$R^4$ is hydrogen or lower-alkyl;
$R^5$ is hydrogen or a residue $R^7$, and
$R^6$ is —$(CH_2)_m R^7$; or
$R^5$ and $R^6$ together with the N atom associated with them is a heterocyclic residue;
$R^7$ is phenyl, substituted phenyl, cycloalkyl, heterocyclyl, lower-alkyl, cyano-lower-alkyl, hydroxy-lower-alkyl, di-lower-alkylamino-lower-alkyl, carboxy-lower-alkyl, lower-alkoxycarbonyl-lower-alkyl, lower-alkoxycarbonylamino-lower-alkyl or phenyl-lower-alkoxycarbonyl;
$R^a$ is hydrogen, lower-alkyl or hydroxy;
$R^b$ is hydrogen or lower-alkyl;
Z is hydroxy, amino or a residue —$OR^8$, —$OC(O)NHR^8$, —$OC(O)OR^8$, —$NHC(O)NHR^8$ or —$NHC(O)OR^8$;
$R^8$ is heterocyclyl, phenyl, substituted phenyl or lower-alkyl;
A and Y each independently is oxygen or sulphur,
X is nitrogen or CH;
m is 0, 1 or 2; and
n is 0, 1 or 2;
or a pharmaceutically usable salt thereof
which process comprises
reacting a compound of formula:

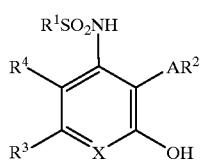
III wherein $R^1$–$R^4$, A and X have the significance given above,
with a compound of the formula HalCH$_2$(CR$^a$R$^b$)$_n$CH$_2$OH, in which Hal is halogen and the hydroxy group(s) contained in the last-named compound can be present in protected form, in the presence of a base.

24. A process for making a compound of the formula,

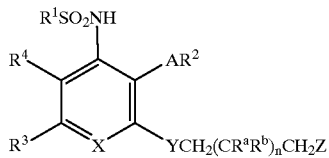

I wherein
- $R^1$ is phenyl, substituted phenyl or heterocyclyl;
- $R^2$ is phenyl or substituted phenyl;
- $R^3$ is hydrogen, lower-alkyl, cyano, carboxy, esterified carboxy, phenyl, substituted phenyl, heterocyclyl or a residue —$CONR^5R^6$ or —$NR^5COR^7$;
- $R^4$ is hydrogen or lower-alkyl;
- $R^5$ is hydrogen or a residue $R^7$, and
- $R^6$ is —$(CH_2)_m R^7$; or
- $R^5$ and $R^6$ together with the N atom associated with them is a heterocyclic residue;
- $R^7$ is phenyl, substituted phenyl, cycloalkyl, heterocyclyl, lower-alkyl, cyano-lower-alkyl, hydroxy-lower-alkyl, di-lower-alkylamino-lower-alkyl, carboxy-lower-alkyl, lower-alkoxycarbonyl-lower-alkyl, lower-alkoxycarbonylamino-lower-alkyl or phenyl-lower-alkoxycarbonyl;
- $R^a$ is hydrogen, lower-alkyl or hydroxy;
- $R^b$ is hydrogen or lower-alkyl;
- Z is hydroxy, amino or a residue —$OR^8$, —$OC(O)NHR^8$, —$OC(O)OR^8$, —$NHC(O)NHR^8$ or —$NHC(O)OR^8$;
- $R^8$ is heterocyclyl, phenyl, substituted phenyl or lower-alkyl;
- A and Y each independently is oxygen or sulphur,
- X is nitrogen or CH;
- m is 0, 1 or 2; and
- n is 0, 1 or 2;

or a pharmaceutically usable salt thereof
which process comprises
treating a compound of formula:

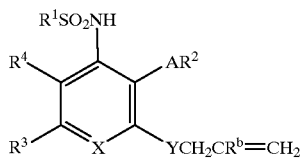

IV wherein $R^1$–$R^4$, $R^b$, A, X and Y have the significance given above,
with an oxidizing agent.

* * * * *